United States Patent
Koizumi

(10) Patent No.: US 11,826,229 B2
(45) Date of Patent: Nov. 28, 2023

(54) FIBROUS SHEET

(71) Applicant: KURARAY CO., LTD., Kurashiki (JP)

(72) Inventor: Satoshi Koizumi, Okayama (JP)

(73) Assignee: KURARAY CO., LTD., Kurashiki (JP)

( * ) Notice: Subject to any disclaimer, the term of this patent is extended or adjusted under 35 U.S.C. 154(b) by 20 days.

(21) Appl. No.: 16/896,679

(22) Filed: Jun. 9, 2020

(65) Prior Publication Data
US 2020/0297542 A1 Sep. 24, 2020

Related U.S. Application Data

(62) Division of application No. 15/577,488, filed as application No. PCT/JP2016/065596 on May 26, 2016, now abandoned.

(30) Foreign Application Priority Data

| May 29, 2015 | (JP) | 2015-110007 |
| May 29, 2015 | (JP) | 2015-110008 |
| May 29, 2015 | (JP) | 2015-110009 |

(51) Int. Cl.
*D04H 1/4391* (2012.01)
*A61F 13/00* (2006.01)
(Continued)

(52) U.S. Cl.
CPC ........ *A61F 13/00038* (2013.01); *A61F 13/00* (2013.01); *A61F 13/00017* (2013.01);
(Continued)

(58) Field of Classification Search
CPC .............. A61F 13/00; A61F 13/00038; A61F 13/00017; A61F 13/105; D04H 1/43918; D04H 1/4391; D04H 1/06; D04H 1/74
See application file for complete search history.

(56) References Cited

U.S. PATENT DOCUMENTS 6,805,961 B1  10/2004  Watanabe et al.
2006/0246803 A1  11/2006  Smith et al.
(Continued)

FOREIGN PATENT DOCUMENTS

| CN | 101522972 A | 9/2009 |
| CN | 106661790 A | 5/2017 |
(Continued)

OTHER PUBLICATIONS

"JP2009097133_Machine Translation" is a machine translation of JP-2009097133-A. (Year: 2009).*
(Continued)

*Primary Examiner* — Larissa Rowe Emrich
(74) *Attorney, Agent, or Firm* — Oblon, McClelland, Maier & Neustadt, L.L.P.

(57) ABSTRACT

Provided are a fibrous sheet having a stress relaxation rate defined by the following formula of less than or equal to 85%:

$$\text{stress relaxation rate [\%]} = (\text{stress } S_5 \text{ at extension after five minutes}/\text{stress } S_0 \text{ at initial extension}) \times 100$$

when a stress at extension immediately after extension in an in-plane first direction at 50% elongation is defined as a stress $S_0$ (N/50 mm) at initial extension, and a stress at extension at a time of extending in the first direction at 50% elongation for five minutes is defined as a stress $S_5$ (N/50 mm) at extension after five minutes, and a bandage including the fibrous sheet.

9 Claims, 3 Drawing Sheets

(a)

(b)

(51) Int. Cl.
*D04H 3/16* (2006.01)
*B32B 5/02* (2006.01)
*B32B 5/26* (2006.01)
*D04H 1/06* (2012.01)
*D04H 1/74* (2006.01)
*A61F 13/10* (2006.01)

(52) U.S. Cl.
CPC ............... *B32B 5/022* (2013.01); *B32B 5/26* (2013.01); *D04H 1/06* (2013.01); *D04H 1/43918* (2020.05); *D04H 1/74* (2013.01); *D04H 3/16* (2013.01); *A61F 13/105* (2013.01); *B32B 2250/03* (2013.01); *B32B 2250/20* (2013.01); *B32B 2250/40* (2013.01); *B32B 2262/0284* (2013.01); *B32B 2262/0292* (2013.01); *B32B 2307/51* (2013.01); *B32B 2535/00* (2013.01); *D10B 2331/04* (2013.01); *D10B 2401/061* (2013.01); *D10B 2509/028* (2013.01)

(56) References Cited

U.S. PATENT DOCUMENTS

| | | | |
|---|---|---|---|
| 2008/0243044 A1 | 10/2008 | Hunt et al. | |
| 2010/0035500 A1* | 2/2010 | Kimura | A61F 13/0273 442/353 |
| 2011/0250390 A1 | 10/2011 | Terada et al. | |
| 2015/0238365 A1* | 8/2015 | Pernot | D04H 1/43832 602/45 |
| 2017/0247823 A1 | 8/2017 | Koizumi et al. | |
| 2017/0275792 A1 | 9/2017 | Kasahara et al. | |
| 2017/0370038 A1 | 12/2017 | Koizumi et al. | |

FOREIGN PATENT DOCUMENTS

| | | | |
|---|---|---|---|
| CN | 106795671 A | 5/2017 | |
| CN | 107109736 A | 8/2017 | |
| EP | 2 058 424 A1 | 5/2009 | |
| EP | 3 184 681 A1 | 6/2017 | |
| EP | 3 187 634 A1 | 7/2017 | |
| EP | 3 239 377 A1 | 11/2017 | |
| JP | 58-87875 U | 6/1983 | |
| JP | 1-176420 U | 12/1989 | |
| JP | 2-59517 A | 2/1990 | |
| JP | 7-62154 A | 3/1995 | |
| JP | 8-92851 A | 4/1996 | |
| JP | 9-13257 A | 1/1997 | |
| JP | 3051373 U | 8/1998 | |
| JP | 11-131346 A | 5/1999 | |
| JP | H11131346 A * | 5/1999 | |
| JP | 11-158732 A | 6/1999 | |
| JP | 11-279912 A | 10/1999 | |
| JP | 2000-217858 | 8/2000 | |
| JP | 2003-509565 | 3/2003 | |
| JP | 2004-83425 A | 3/2004 | |
| JP | 2004-141613 A | 5/2004 | |
| JP | 2005-42290 A | 2/2005 | |
| JP | 2005-95381 A | 4/2005 | |
| JP | 2005-177176 A | 7/2005 | |
| JP | 3743966 B2 | 2/2006 | |
| JP | 2007-21068 | 2/2007 | |
| JP | 2007-275357 A | 10/2007 | |
| JP | 2008-539106 A | 11/2008 | |
| JP | 2009-097133 A | 5/2009 | |
| JP | 2009097133 A * | 5/2009 | ........... D01D 5/0069 |
| JP | 2010-270407 A | 12/2010 | |
| JP | 2011-32631 A | 2/2011 | |
| JP | 2011-125730 A | 6/2011 | |
| JP | 2011-184846 A | 9/2011 | |
| JP | 2011-219900 A | 11/2011 | |
| JP | 2013-32382 A | 2/2013 | |
| JP | 2013-36151 A | 2/2013 | |
| JP | 2014-4066 A | 1/2014 | |
| JP | 2014-37649 A | 2/2014 | |
| JP | 2014-37662 A | 2/2014 | |
| JP | 2014037649 A * | 2/2014 | |
| JP | 2014037662 A * | 2/2014 | |
| JP | 2014-515320 A | 6/2014 | |
| JP | 2014-194089 A | 10/2014 | |
| JP | 5600119 B2 | 10/2014 | |
| KR | 10-2009-0048457 | 5/2009 | |
| TW | 200824655 A | 6/2008 | |
| WO | WO 01/19920 A1 | 3/2001 | |
| WO | 2006/118838 A2 | 11/2006 | |
| WO | 2008/015972 A1 | 2/2008 | |
| WO | WO 2008/139601 A1 | 11/2008 | |
| WO | 2010/077929 A1 | 7/2010 | |
| WO | 2012/158879 A1 | 11/2012 | |

OTHER PUBLICATIONS

"JP2014037649_Machine Translation" is a machine translation of JP-2014037649-A. (Year: 2014).*
"JP2014037662_Machine Translation" is a machine translation of JP-2014037662-A. (Year: 2014).*
"JPH11131346_Machine Translation" is a machine translation of JPH11131346A. (Year: 1999).*
Office Action dated Sep. 4, 2020, in co-pending U.S. Appl. No. 15/577,488.
Office Action dated Jun. 5, 2018 in Japanese Patent Application No. 2015-110009 with English translation, citing document AO therein, 12 pages.
Extended European Search Report dated Nov. 29, 2018 in European Patent Application No. 16803208.4, citing documents AO through AR therein, 12 pages.
Combined Office Action and Search Report dated Jul. 3, 2019 in Chinese Patent Application No. 201680038235.7, citing documents AO-AR therein, 25 pages (with English translation).
Taiwanese Office Action and Search Report dated Dec. 17, 2019, in Patent Application No. 105116660, citing documents AO-AP therein, 27 pages (with English translation).
Information Offer Form issued Sep. 11, 2018 in Japanese Patent Application No. 2015-110007 (with English translation), citing documents AH through AK therein, 9 pages.
Japanese Office Action dated Sep. 5, 2018 in Japanese Patent Application No. 2015-110007 (with English translation), citing documents AL, AM and AN therein, 12 pages.
Japanese Office Action dated Sep. 5, 2018 in Japanese Patent Application No. 2015-110008 (with English translation), citing documents AH, and AO through AR therein, 12 pages.
Japanese Office Action dated Sep. 5, 2018 in Japanese Patent Application No. 2015-110009 (with English translation), citing documents AS, AT and AU therein, 12 pages.
International Search Report dated Aug. 2, 2016, in PCT/JP2016/065596, filed May 26, 2016.
Office Action dated Jun. 8, 2022 in Indian Patent Application No. 202118055295, filed Nov. 29, 2021.
Office Action dated Jun. 30, 2022 in Korean Patent Application No. 10-2017-7037208, filed May 26, 2016 w/English translation.
Korean Office Action dated Oct. 20, 2022 in Korean Patent Application No. 10-2017-7037208 (with English Translation), citing reference 15 therein, 3 pages.

* cited by examiner

FIG.1
(a)
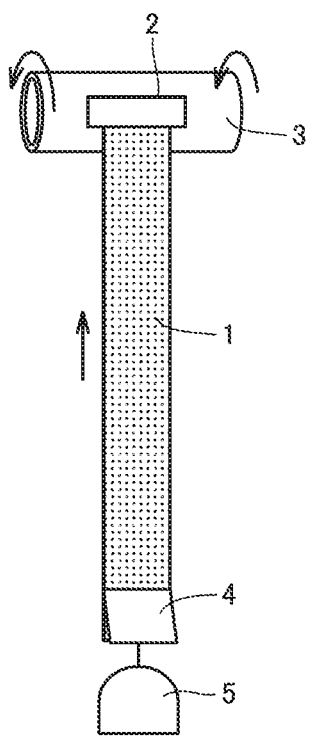
(b)
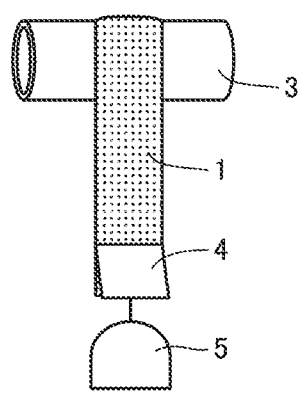

FIBROUS SHEET

CROSS REFERENCE TO RELATED APPLICATIONS

The present application is a divisional of U.S. patent application Ser. No. 15/577,488, filed on Nov. 28, 2017, which is a 35 U.S.C. § 371 national stage patent application of international patent application PCT/JP2016/065596, filed on May 26, 2016, which claims priority to Japanese patent applications JP 2015-110007, filed on May 29, 2015, JP2015-110008, filed on May 29, 2015 and JP 2015-110009, filed on May 29, 2015.

TECHNICAL FIELD

The present invention relates to a fibrous sheet suitably usable as a bandage or the like.

BACKGROUND ART

A bandage is used not only to directly protect an application site such as an affected part by being wrapped around the application site, or to fix another protective member (such as a gauze) to the application site, but also, when the bandage has stretchability, to stop bleeding of a wound site by a compression force using its stretchability at the time of wrapping and to improve swelling by promoting a blood flow. In recent years, a bandage has been applied to compression therapy where treatment is carried out by compressing an affected part, such as treatment and improvement of lower extremity varicose veins.

As a method of imparting stretchability to a bandage, there have been known 1) a method of weaving, into a fabric, yarn formed of a stretchable material such as an elastomer typified by rubber and 2) a method of combining a layer formed of a stretchable material such as an elastomer with a nonstretchable fabric or impregnating a nonstretchable fabric with a stretchable material, and many stretchable bandages produced by using such methods are commercially available.

For example, Japanese Patent No. 3743966 (PTD 1) discloses a stretchable bandage imparted with stretchability in the longitudinal direction by including elastic yarn for warp. Japanese Patent No. 5600119 (PTD 2) discloses an elastic nonwoven fabric fibrous web imparted with stretchability by a method of entangling a nonwoven fabric fiber with an extended elastic filament and then relaxing the extended state of the elastic filament. Japanese National Patent Publication No. 2014-515320 (PTD 3) discloses a stretchable self-adherent composite article obtained by impregnating an elastic composite article that includes a nonwoven fibrous coverweb, a woven scrim, and a plurality of elastic yarns located between the coverweb and the woven scrim, with an elastomeric polymeric binder.

CITATION LIST

Patent Document

PTD 1: Japanese Patent No. 3743966
PTD 2: Japanese Patent No. 5600119
PTD 3: Japanese National Patent Publication No. 2014-515320

SUMMARY OF INVENTION

Technical Problems

In a conventional stretchable bandage formed by combining elastomer materials such as a rubber yarn, there have been problems such as blood circulation disturbance or a feeling of pain when such a bandage is wrapped around an application site for a long time. Such a problem can be suppressed by reducing tensile stress of the materials constituting the bandage. However, when a bandage with small tensile stress is used, there is a tendency for the bandage to be wrapped around an application site with strong tension in order to firmly fix the bandage to the application site, so that this may rather aggravate the above-described problem.

When a bandage is applied to a site to be bent and stretched, such as a joint part, it is certainly advantageous that the bandage has stretchability in view of increasing the ease of bending (movability) of the joint part. However, there has been still room for improvement in the ease of bending of the joint part, in particular the ease of bending of small joint parts such as fingers.

A bandage can be applied to every part of the body. Accordingly, when the conventional bandage having stretchability is wrapped around a site having surface protrusions and recesses, such as a joint part, the bandage can be wrapped along a surface in the vicinity of the peaks of the protrusions and has good adhesion to the surface; however, the wrapped bandage does not satisfactorily follow the surface at its periphery (recesses), so that the bandage may float from the surface. In this specification, when a sheet such as a bandage is wrapped around a site having surface protrusions and recesses, the property of being able to be wrapped along the shapes of the surface protrusions and recesses is referred to as a "concavo-convex fitting property".

When a bandage is inferior in the concavo-convex fitting property, floating of the wrapped bandage may occur as described above, and in this case, the bandage is apt to become loose and is unwrapped, or a desired compression force cannot be obtained in some cases. When a bandage is wrapped with strong tension to follow surface protrusions and recesses, there occur problems such as blood circulation disturbance or a feeling of pain due to seaming.

A first object of the present invention is to provide an extensible fibrous sheet capable of suppressing problems such as blood circulation disturbance and pain even when the fibrous sheet is wrapped around an application site for a long time, and a bandage including the fibrous sheet.

A second object of the present invention is to provide a fibrous sheet less liable to disturb the bending motion of a site to be bent and stretched, such as a joint part, even when the fibrous sheet is wrapped around the site, and a bandage including the fibrous sheet.

A third object of the present invention is to provide a fibrous sheet having a good concavo-convex fitting property and capable of being wrapped along the shape of surface protrusions and recesses even when wrapped with moderate strength, and a bandage including the fibrous sheet.

Solutions to Problems

In order to achieve the first object, the present invention provides a fibrous sheet and a bandage described below.

[1] A fibrous sheet having a stress relaxation rate defined by a formula below of less than or equal to 85%:

stress relaxation rate [%]=(stress $S_5$ at extension after five minutes/stress $S_0$ at initial extension)×100 when a stress at extension immediately after extension in an in-plane first direction at 50% elongation is defined as a stress $S_0$(N/50 mm) at initial extension, and a stress at extension at a time of extending in the first direction at 50% elongation for five minutes is defined as a stress $S_3$ (N/50 mm) at extension after five minutes.

[2] The fibrous sheet described in [1],
wherein the stress relaxation rate is greater than or equal to 65%.

[3] The fibrous sheet described in [1] or [2],
wherein the stress $S_0$ at initial extension is from 2 to 30 N/50 mm.

[4] The fibrous sheet described in any one of [1] to [3],
wherein the fibrous sheet has a curved surface sliding stress of 5 to 30 N/50 mm.

[5] The fibrous sheet described in any one of [1] to [4],
wherein the fibrous sheet has a length direction and a width direction, and
the first direction is the length direction.

[6] The fibrous sheet described in any one of [1] to [5],
wherein the fibrous sheet is a nonwoven fabric sheet.

[7] The fibrous sheet described in any one of [1] to [6],
wherein the fibrous sheet is a bandage.

In order to achieve the second object, the present invention provides a fibrous sheet and a bandage described below.

[8] A fibrous sheet that satisfies a formula below:

$\{T_3/(3 \times T_1)\} \times 100 \leq 85 [\%]$ when a thickness of a single fibrous sheet measured in accordance with A method specified in JIS L 1913 is defined as $T_1$ [mm], and a thickness of three superimposed sheets measured under the same conditions is defined as $T_3$ [mm].

[9] The fibrous sheet described in [8],
wherein the fibrous sheet satisfies a formula below:

$S_2/S_1 \geq 3$ when a stress at extension at a time of extension in an in-plane first direction at 50% elongation is defined as a stress $S_1$ (N/50 mm) at 50% extension, and a stress at extension at a time of extension in an in-plane second direction orthogonal to the first direction at 50% elongation is defined as a stress $S_2$ (N/50 mm) at 50% extension.

[10] The fibrous sheet described in [9],
wherein the fibrous sheet has a length direction and a width direction, and
the first direction is the width direction.

[11] The fibrous sheet described in any one of [8] to [10],
wherein the fibrous sheet has a basis weight of greater than or equal to 50 g/m².

[12] The fibrous sheet described in any one of [8] to [11],
wherein the fibrous sheet has a compression elastic modulus measured in accordance with JIS L 1913 of less than or equal to 85%.

[13] The fibrous sheet described in any one of [8] to [12],
wherein the fibrous sheet has a curved surface sliding stress of 3 to 30 N/50 mm.

[14] The fibrous sheet described in any one of [8] to [13],
wherein the fibrous sheet is a nonwoven fabric sheet.

[15] The fibrous sheet described in [14],
wherein the fibrous sheet includes crimped fibers.

[16] The fibrous sheet described in any one of [8] to [15],
wherein the fibrous sheet is a bandage.

In order to achieve the third object, the present invention provides a fibrous sheet and a bandage described below.

[17] A fibrous sheet having a length direction and a width direction,
wherein a bending resistance in the width direction measured in accordance with Handle-o-Meter method specified in JIS L 1913 is less than or equal to 300 mN/50 mm.

[18] The fibrous sheet described in [17],
wherein the bending resistance in the width direction is lower than a bending resistance in the length direction.

[19] The fibrous sheet described in [17] or [18],
wherein the fibrous sheet has a compression elastic modulus measured in accordance with JIS L 1913 of less than or equal to 85%.

[20] The fibrous sheet described in any one of [17] to [19],
wherein the fibrous sheet has a curved surface sliding stress of 3 to 30 N/50 mm.

[21] The fibrous sheet described in any one of [17] to [20],
wherein the fibrous sheet is a nonwoven fabric sheet.

[22] The fibrous sheet described in [21],
wherein fibers constituting the nonwoven fabric sheet have an average fineness of less than or equal to 20 dtex.

[23] The fibrous sheet described in [21] or [22],
wherein the fibrous sheet includes crimped fibers.

[24] The fibrous sheet described in any one of [17] to [23],
wherein the fibrous sheet is a bandage.

Advantageous Effects of Invention

The present invention can provide an extensible fibrous sheet capable of suppressing problems such as blood circulation disturbance and pain even when the fibrous sheet is wrapped around an application site for a long time, and a bandage including the fibrous sheet.

The present invention can provide a fibrous sheet less liable to disturb the bending motion of a site to be bent and stretched, such as a joint part, even when the fibrous sheet is wrapped around the site, and a bandage including the fibrous sheet.

The present invention can provide a fibrous sheet having a good concavo-convex fitting property and a bandage including the fibrous sheet.

BRIEF DESCRIPTION OF DRAWINGS

FIG. 1 is a schematic diagram showing a method of preparing a sample for measuring curved surface sliding stress.

DESCRIPTION OF EMBODIMENTS

Figure 2:
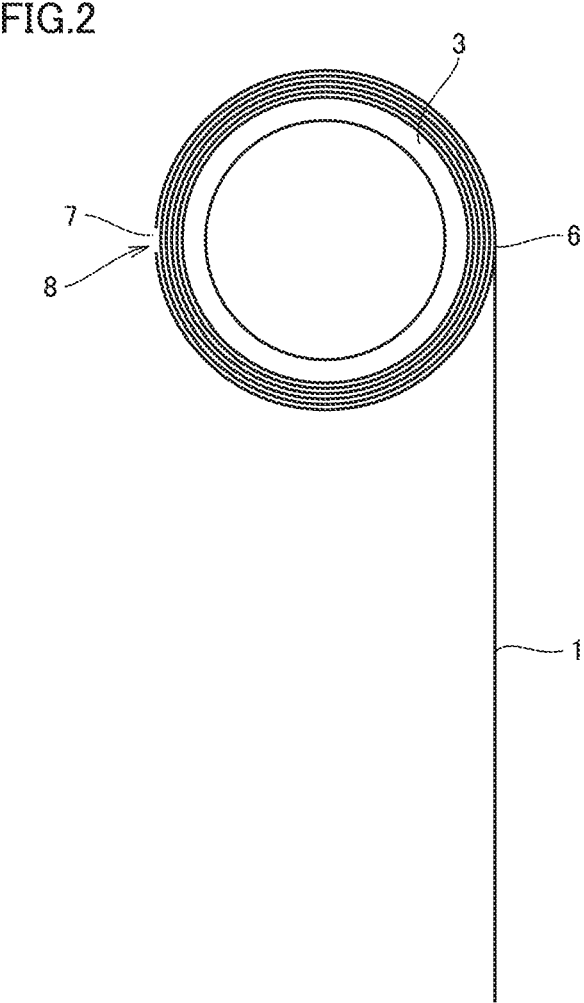
FIG. 2 is a cross-sectional schematic diagram showing the sample for measuring the curved surface sliding stress.

First Embodiment (1) Characteristics of Fibrous Sheet

A fibrous sheet according to the present embodiment (hereinafter also simply referred to as a "fibrous sheet") is an extensible fibrous sheet capable of being suitably used not only as a general bandage but also as a medical article such as a compression bandage used for hemostasis, compression therapy, and so on. In the present specification, "extensible/having extensibility" means that a stress at 50% extension is exhibited in at least one direction (first direction) in the sheet plane, and the stress at 50% extension is preferably greater than or equal to 0.1 N/50 mm, more preferably greater than or equal to 0.5 N/50 mm, further preferably greater than or equal to 1 N/50 mm.

The stress at 50% extension means stress at extension immediately after extension in the first direction at 50% elongation, and in the present specification, this stress is also referred to as "stress $S_0$ at initial extension" [unit: N/50 mm]. The stress $S_0$ at initial extension is measured by a tensile test in accordance with the "Test methods for nonwovens" specified in JIS L 1913. The stress $S_0$ at initial extension is preferably less than or equal to 30 N/50 mm, more preferably less than or equal to 20 N/50 mm, further preferably less than or equal to 15 N/50 mm. The stress $S_0$ at initial extension being less than or equal to 30 N/50 mm is advantageous for suppressing problems such as blood circulation disturbance and pain that may occur when the sheet is wrapped around an application site for a long time.

The first direction of the fibrous sheet may be a flow direction (MD direction) of the fibrous sheet in a production process, and when the fibrous sheet has, for example, a length direction and a width direction like a bandage, the first direction is preferably the length direction of the fibrous sheet. In this case, the fibrous sheet as a bandage is wrapped around an application site while extending along the length direction thereof. When the fibrous sheet has a length direction and a width direction, a CD direction orthogonal to the MD direction is preferably the width direction.

The stress at 50% extension in a direction other than the first direction in the fibrous sheet, for example, the CD direction, or a width direction when the fibrous sheet has a length direction and the width direction like a bandage is, for example, 0.5 to 50 N/50 mm, and preferably 1 to 30 N/50 mm.

When a stress at extension at the time of extending in the first direction at 50% elongation for five minutes is defined as a stress $S_5$ (N/50 mm) at extension after five minutes, a stress relaxation rate defined by the following formula:

Stress relaxation rate [%]=(stress $S_5$ at extension after five minutes/stress $S_0$ at initial extension)×100 is less than or equal to 85%.

The "stress at extension at the time of extending in the first direction at 50% elongation for five minutes" means a stress at extension generated when the sheet is extended in the first direction at 50% elongation and held in this state for five minutes. Similarly to the stress $S_0$ at initial extension, it is measured by a tensile test in the "Test methods for nonwovens" specified in JIS L 1913.

According to the fibrous sheet having a stress relaxation rate of less than or equal to 85%, it is possible to effectively suppress problems such as blood circulation disturbance and pain that may occur when the sheet is wrapped around an application site for a long time. That is, according to the fibrous sheet, the tensile stress of the fibrous sheet is moderately relaxed with time as the fibrous sheet is wrapped around the application site, so that the above-described problems caused by seaming are less likely to occur. The stress relaxation rate is preferably less than or equal to 84%, more preferably less than or equal to 83%.

The stress relaxation rate is preferably greater than or equal to 65%, more preferably greater than or equal to 70%, further preferably greater than or equal to 75%. When the stress relaxation rate is within this range, it is possible to suppress occurrence of displacement and peeling of the wrapped fibrous sheet due to gradual loosening of the wrapped state after the fibrous sheet is wrapped around an application site.

The fibrous sheet preferably exhibits self-adhesiveness. In the present specification, the "self-adhesiveness" refers to a property allowing fibers on a fibrous sheet surface to engage with each other or come into close contact with each other due to superposition (contact) of the fibers and to be hooked or fixed. The fibrous sheet having self-adhesiveness is advantageous when the fibrous sheet is a bandage or the like. For example, in the case where the fibrous sheet is a bandage, after the bandage is wrapped around an application site, the wrapped fibrous sheets are pressed against each other while being extended by such an operation that an end of the bandage is overlapped on (or torn and then overlapped on) a bandage surface located under the end, so that the fibrous sheets are joined and fixed to each other, thereby expressing self-adhesiveness.

When the fibrous sheet itself has self-adhesiveness, it is unnecessary to form a layer formed of a self-adhesive agent such as an elastomer or a pressure-sensitive adhesive on a surface of the fibrous sheet or to prepare separately a fastener for fixing the tip after wrapping. It is preferable that the fibrous sheet is constituted only of a non-elastomer material. More specifically, it is preferable that the fibrous sheet is constituted only of fibers. For example, Japanese Patent Laying-Open No. 2005-095381 (PTD 4) describes that an acrylic polymer (claim 1) or a latex (paragraphs [0004] to [0006]) is caused to adhere as a self-adhesive agent to at least one side of a bandage base material. However, when such a layer formed of an elastomer is formed on the fibrous sheet surface, this may cause problems such as blood circulation disturbance and pain when the sheet is wrapped around an application site for a long time. The layer formed of an elastomer may induce skin irritation and allergy when wrapped around an application site.

Figure 3:
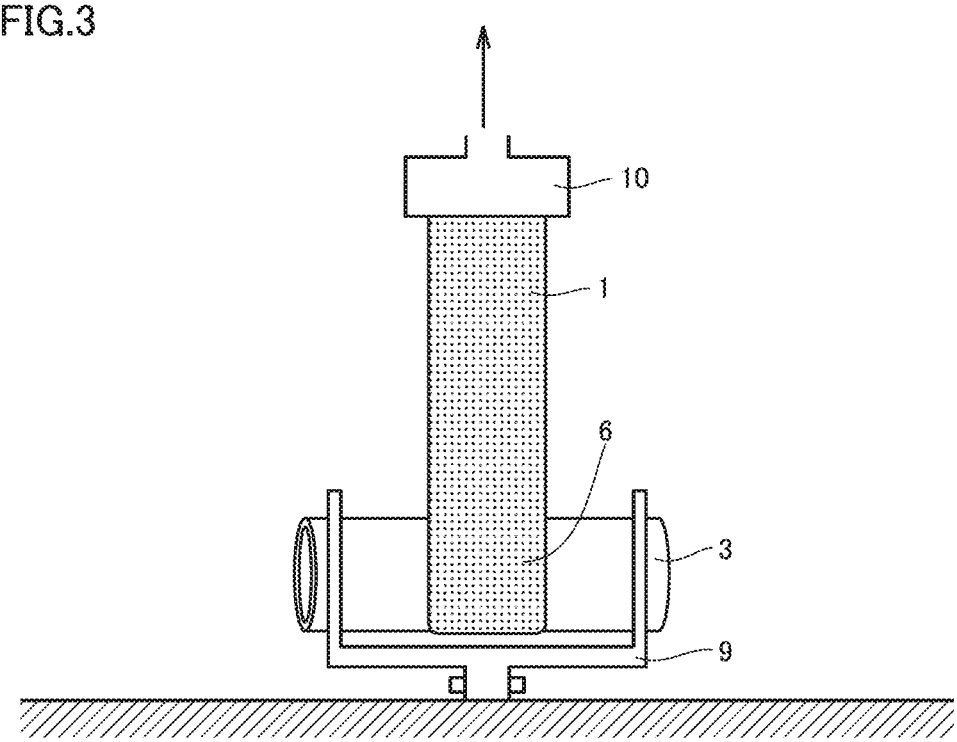
FIG. 3 is a schematic diagram showing a method of measuring the curved surface sliding stress.

The self-adhesiveness of the fibrous sheet can be evaluated by a curved surface sliding stress. From the viewpoint of the self-adhesiveness, it is preferable that the fibrous sheet has a curved surface sliding stress of, for example, greater than or equal to 3 N/50 mm, preferably greater than or equal to 5 N/50 mm, and the curved surface sliding stress is preferably higher than breaking strength. Since it is relatively easy to unwrap the wrapped fibrous sheet if desired, the curved surface sliding stress is preferably less than or equal to 30 N/50 mm, more preferably less than or equal to 25 N/50 mm. The curved surface sliding stress is measured using a tensile tester in accordance with the method described in Examples section (FIGS. 1 to 3).

The fibrous sheet preferably has a hand cut property. In the present specification, the "hand cut property" refers to a property enabling breakage (cutting) by hand tension. The hand cut property of the fibrous sheet can be evaluated by breaking strength. From the viewpoint of the hand cut property, the fibrous sheet has a breaking strength in at least one direction in the sheet plane of preferably 5 to 100 N/50 mm, more preferably 8 to 60 N/50 mm, further preferably 10 to 40 N/50 mm. When the breaking strength is within the above range, it is possible to impart a good hand cut property enabling relatively easy breakage (cutting) by hand. If the breaking strength is too large, the hand cut property deteriorates, making it difficult to cut the fibrous sheet with one hand, for example. On the other hand, if the breaking strength is too small, the strength of the fibrous sheet becomes insufficient to cause easy breakage of the fibrous sheet, and durability and handleability are lowered. The breaking strength is measured by a tensile test in accordance with the "Test methods for nonwovens" specified in JIS L 1913.

At least one direction in the sheet plane is a tensile direction when the fibrous sheet is cut by hand, and is preferably the above-described first direction. The first direction may be the MD direction, and when the fibrous sheet has, for example, a length direction and a width direction like a bandage, the first direction is preferably the length direction of the fibrous sheet. That is, when the fibrous sheet is used as a bandage, it is usual to break the bandage in the length direction after the bandage is wrapped around an application site while being extended along the length direction thereof, and therefore the first direction is preferably the length direction as the tensile direction.

The breaking strength in a direction other than at least one direction in the sheet plane, for example, the CD direction, or a width direction when the fibrous sheet has a length direction and the width direction like a bandage is, for example, 0.1 to 300 N/50 mm, preferably 0.5 to 100 N/50 mm, more preferably 1 to 20 N/50 mm.

From the viewpoint of the hand cut property, it is preferable that the fibrous sheet is constituted only of a non-elastomer material. More specifically, it is preferable that the fibrous sheet is constituted only of fibers. If a layer formed of an elastomer, etc. is formed on the fibrous sheet surface, the hand cut property may be lowered.

The fibrous sheet has an elongation at break in at least one direction in the sheet plane of, for example, greater than or equal to 50%, preferably greater than or equal to 60%, more preferably greater than or equal to 80%. When the elongation at break is within the above range, it is advantageous for enhancing the stretchability of the fibrous sheet. In the case where the fibrous sheet is used as a bandage, the followability can be enhanced when the fibrous sheet is applied to a site with large movement, such as a joint. The elongation at break in at least one direction in the sheet plane is usually less than or equal to 300% and preferably less than or equal to 250%. The elongation at break is also measured by a tensile test in accordance with the "Test methods for nonwovens" specified in JIS L 1913.

At least one direction in the sheet plane is preferably the above-described first direction. The first direction may be the MD direction, and when the fibrous sheet has, for example, a length direction and a width direction like a bandage, the first direction is preferably the length direction of the fibrous sheet.

The elongation at break in a direction other than at least one direction in the sheet plane, for example, the CD direction, or a width direction when the fibrous sheet has a length direction and the width direction like a bandage is, for example, 10 to 500%, preferably 100 to 350%.

The fibrous sheet has a recovery rate after 50% extension in at least one direction in the sheet plane (recovery rate after 50% extension) is preferably greater than or equal to 70% (less than or equal to 100%), more preferably greater than or equal to 80%, further preferably greater than or equal to 90%. When the recovery rate after 50% extension is within the range, the followability to extension is enhanced, and for example when the sheet is used as a bandage, the bandage satisfactorily follows the shape of a portion around which the bandage is wrapped, and at the same time, it is advantageous for improvement of the self-adhesiveness due to friction between the overlapped fibrous sheets. When the extension recovery rate is excessively small, the fibrous sheet cannot follow movement of a portion around which the fibrous sheet is to wrapped in the case where the portion has a complex shape or moves during use of the fibrous sheet, and a portion deformed by body movement does not return to its original shape, thus weakening fixation of the wrapped fibrous sheet.

At least one direction in the sheet plane is preferably the above-described first direction. The first direction may be the MD direction, and when the fibrous sheet has, for example, a length direction and a width direction like a bandage, the first direction is preferably the length direction of the fibrous sheet.

The recovery rate after 50% extension is defined by the following formula:

$$\text{Recovery rate after 50\% extension (\%)} = 100 - X$$

when, in a tensile test in accordance with the "Test methods for nonwovens" specified in JIS L 1913, a residual strain (%) after the test is defined as $X$ when load is removed immediately after the elongation rate reaches 50%.

The recovery rate after 50% extension in a direction other than at least one direction in the sheet plane, for example, the CD direction, or a width direction when the fibrous sheet has a length direction and the width direction like a bandage is, for example, greater than or equal to 70% (less than or equal to 100%), preferably greater than or equal to 80%.

The fibrous sheet has a basis weight of preferably 30 to 300 $g/m^2$, more preferably 50 to 200 $g/m^2$. The fibrous sheet has a thickness of: for example, 0.2 to 5 mm, preferably 0.3 to 3 mm, more preferably 0.4 to 2 mm. When the basis weight and the thickness are within these ranges, a balance between the stretchability and the flexibility, touch feeling or cushioning property of the fibrous sheet is good. A density (bulk density) of the fibrous sheet can be a value corresponding to the above-described basis weight and thickness, and the density (bulk density) is, for example, 0.03 to 0.5 $g/cm^3$, preferably 0.04 to 0.4 $g/cm^3$, more preferably 0.05 to 0.2 $g/cm^3$.

The fibrous sheet has an air permeability measured by the Frazier method of preferably greater than or equal to 0.1 $cm^3/(cm^2 \cdot second)$, more preferably 1 to 500 $cm^3/(cm^2 \cdot second)$, further preferably 5 to 300 $cm^3/(cm^2 \cdot second)$, particularly preferably 10 to 10 to 200 $cm^3/(cm^2*second)$. When the air permeability is within this range, the fibrous sheet is more suitably used for the human body, such as a bandage, because the fibrous sheet is good in air permeability and is hardly stuffy.

(2) Structure and Production Method of Fibrous Sheet

The fibrous sheet of the present embodiment is not particularly limited as long as it is constituted of fibers, and the fibrous sheet may be, for example, a woven fabric, a nonwoven fabric, a knit (knitted fabric), or the like. Although the shape of the fibrous sheet can be selected according to use application, it is preferably a rectangular sheet shape having a length direction and a width direction such as a tape shape or a belt shape (long shape). The fibrous sheet may have a single layer structure or a multilayer structure including two or more fibrous layers.

As means for imparting stretchability and extensibility to the fibrous sheet, there are 1) a method of subjecting a fibrous sheet substrate such as a woven fabric, a nonwoven fabric, or a knit to gathering, and 2) a method using crimped fibers crimped into a coil shape as at least some fibers constituting a nonwoven fabric. As described above, the method of weaving, into a fibrous sheet, yarn formed of a stretchable material such as an elastomer typified by rubber and the method of combining a layer formed of a stretchable material such as an elastomer with a nonstretchable fibrous sheet substrate or impregnating a nonstretchable fibrous sheet substrate with a stretchable material cause problems such as blood circulation disturbance and pain when the fibrous sheet is wrapped around an application site for a long time.

From the viewpoint of self-adhesiveness, hand cut property, ease of bending of a joint exhibited when the fibrous sheet is wrapped around the joint, conformity (fitting property) with a concavo-convex site such as a joint exhibited when the fibrous sheet is wrapped around the concavo-convex site, etc., the fibrous sheet is preferably constituted of a nonwoven fabric, namely, the fibrous sheet is preferably a nonwoven fabric sheet. More preferably, the fibrous sheet is constituted of a nonwoven fabric containing crimped fibers crimped into a coil shape, and still more preferably, the fibrous sheet is constituted of a nonwoven fabric that contains the crimped fibers and that is an ungathered nonwoven fabric. Particularly preferably, the nonwoven fabric sheet is constituted only of the crimped fibers.

It is preferable that the fibrous sheet constituted of the nonwoven fabric containing the crimped fibers has a structure in which the respective fibers constituting this nonwoven fabric are not substantially fusion-bonded, but mainly the crimped fibers are entangled with each other at their crimped coil portions and bound or hooked. Further, it is preferable that most (the majority of) crimped fibers (axial direction of crimped fibers) are oriented substantially parallel to a sheet surface. In the present specification, "oriented substantially parallel to a surface direction" means a state where a portion in which a large number of crimped fibers (axial direction of crimped fibers) are locally oriented along a thickness direction is not repeatedly present, as in for example entanglement by needle punching.

In the fibrous sheet constituted of the nonwoven fabric containing the crimped fibers, the crimped fibers are preferably oriented in a certain direction in the sheet plane (for example, in the above-described first direction, preferably in the length direction), and the adjacent or intersecting crimped fibers are entangled with each other at their crimped coil portions. Even in the thickness direction (or oblique direction) of the fibrous sheet, the crimped fibers are preferably slightly entangled with each other. The entanglement of the crimped fibers can be caused by the process of shrinking a fibrous web as a precursor of the fibrous sheet.

The nonwoven fabric in which crimped fibers (axial direction of crimped fibers) are oriented in a certain direction in the sheet plane and entangled exhibits good stretchability (including extensibility) in this direction. In the case where the certain direction is, for example, the length direction, when a tensile force is applied to the stretchable nonwoven fabric in the length direction, the entangled crimped coil portion tends to extend and return to the original coil shape, so that high stretchability can be exhibited in the length direction. The cushioning property and flexibility in the thickness direction can be expressed by slight entanglement of the crimped fibers in the thickness direction of the nonwoven fabric, whereby the nonwoven fabric can have good touch feeling and texture. The crimped coil portion easily entangles with another crimped coil portion by contact with a certain degree of pressure. The self-adhesiveness can be expressed by the entanglement of the crimped coil portions.

In the fibrous sheet constituted of the nonwoven fabric containing the crimped fibers, when a tensile force is applied to the orientation direction of the crimped fiber (for example, in the above-described first direction, preferably in the length direction), the entangled crimped coil portion extends due to elastic deformation, and when the tensile force is further applied, the fibrous sheet is finally unwrapped, so that the cutting property (hand cut property) is also good.

As described above, the nonwoven fabric capable of constituting the fibrous sheet preferably contains crimped fibers crimped into a coil shape. The crimped fiber is preferably oriented mainly in the surface direction of the nonwoven fabric, and further preferably crimps substantially evenly in the thickness direction. The crimped fiber can be constituted of a conjugated fiber in which a plurality of resins having different thermal shrinkage factors (or thermal expansion coefficients) form a phase structure.

The conjugated fiber constituting the crimped fiber is a fiber (latently crimped fiber) having an asymmetric or layered (so-called bimetal) structure crimped by heating due to a difference in thermal shrinkage factor (or thermal expansion coefficient) of a plurality of resins. The plurality of resins usually have mutually different softening points or melting points. The plurality of resins can be selected from thermoplastic resins such as, for example, polyolefin-based resins (e.g., poly-$C_{2-4}$ olefin-based resins such as low-density, medium-density or high-density polyethylene and polypropylene); acrylic resins (e.g., acrylonitrile-based resins having an acrylonitrile unit, such as acrylonitrile-vinyl chloride copolymers); polyvinyl acetal-based resins (e.g., polyvinyl acetal resins), polyvinyl chloride-based resins (e.g., polyvinyl chloride, vinyl chloride-vinyl acetate copolymers and vinyl chloride-acrylonitrile copolymers); polyvinylidene chloride-based resins (e.g., vinylidene chloride-vinyl chloride copolymers and vinylidene chloride-vinyl acetate copolymers); styrene-based resins (e.g., heat-resistant polystyrene); polyester-based resins (e.g., poly-$C_{2-4}$ alkylene arylate-based resins such as polyethylene terephthalate resins, polytrimethylene terephthalate resins, polybutylene terephthalate resins and polyethylene naphthalate resins); polyamide-based resins (e.g., aliphatic polyamide-based resins such as polyamide 6, polyamide 66, polyamide 11, polyamide 12, polyamide 610 and polyamide 612, semi-aromatic polyamide-based resins, and aromatic polyamide-based resins such as polyphenylene isophthalamide, polyhexamethylene terephthalamide and poly-p-phenylene-terephthalamide); polycarbonate-based resins (e.g., bisphenol A-type polycarbonate); polyparaphenylene benzobisoxazole resins; polyphenylene sulfide resins; polyurethane-based resins, and cellulose-based resins (e.g., cellulose esters). These thermoplastic resins may contain other copolymerizable units.

Among the thermoplastic resins, non thermal adhesive resins under moisture (or heat-resistant hydrophobic resins or nonaqueous resins) having a softening point or melting point greater than or equal to 100° C., such as, for example, polypropylene-based resins, polyester-based resins and polyamide-based resins are preferable because fibers are not melted or softened to be fused even when subjected to a heating treatment with high-temperature steam. Particularly, aromatic polyester-based resins and polyamide-based resins are preferable because they are excellent in balance among heat resistance, fiber formability, and so on. A resin exposed to surfaces of conjugated fibers constituting a nonwoven fabric (latently crimped fiber) is preferably at least a non thermal adhesive resin under moisture so that the conjugated fibers are not fused even when treated with high-temperature steam.

The plurality of resins forming the conjugated fiber may have different thermal shrinkage factors, and may be a combination of resins of the same kind, or a combination of different kinds of resins.

Preferably, the plurality of resins forming the conjugated fiber are a combination of resins of the same kind from the viewpoint of adhesiveness. In the case of the combination of resins of the same kind, usually a combination of a component (A) forming a homopolymer (essential component) and a component (B) forming a modification polymer (copolymer) is used. That is, for example, a copolymerizable monomer for reducing the crystallization degree, the melting point, the softening point, or the like is copolymerized with the homopolymer as an essential component to perform modification, whereby the crystallization degree may be reduced as compared to the homopolymer, or the polymer may be made noncrystalline to reduce the melting point or softening point as compared to the homopolymer. When the crystallization degree, the melting point, or the softening point is changed as described above, this can cause a difference in thermal shrinkage factor. The difference in melting point or softening point is, for example, 5 to 150° C., and preferably 40 to 130° C., more preferably 60 to 120° C. A ratio of the copolymerizable monomer to be used for modification is, for example, 1 to 50 mol %, preferably 2 to 40 mol %, more preferably 3 to 30 mol % (particularly 5 to 20 mol %) based on the whole amount of monomers. While a mass ratio between the component forming a homopolymer and the component forming a modification polymer can be selected according to the structure of fibers, the homopolymer component (A)/the modification polymer component (B) is for example 90/10 to 10/90, and preferably 70/30 to 30/70, more preferably 60/40 to 40/60.

The conjugated fiber is preferably a combination of aromatic polyester-based resins, more preferably a combination of a polyalkylene arylate-based resin (a) and a modified polyalkylene arylate-based resin (b) because latently crimpable conjugated fibers are easily produced. The polyalkylene arylate-based resin (a) can be a homopolymer of an aromatic dicarboxylic acid (e.g., a symmetric aromatic dicarboxylic acid such as terephthalic acid or naphthalene-2,6-dicarboxylic acid) and an alkanediol component (e.g., $C_{2-6}$ alkanediol such as ethylene glycol or butylene glycol). Specifically, a poly-$C_{2-4}$ alkylene terephthalate-based resin such as polyethylene terephthalate (PET) or polybutylene terephthalate (PBT), or the like is used, and usually, PET for use in general PET fibers having an intrinsic viscosity of 0.6 to 0.7 is used.

On the other hand, in the modified polyalkylene arylate-based resin (b), examples of a copolymerization component for reducing the melting point or softening point and the crystallization degree of the polyalkylene arylate-based resin (a) as an essential component include dicarboxylic acid components such as an asymmetric aromatic dicarboxylic acid, an alicyclic dicarboxylic acid and an aliphatic dicarboxylic acid: an alkanediol component having a chain length longer than that of alkanediol of the polyalkylene arylate-based resin (a); and/or an ether bond-containing diol component. The copolymerization components may be used singly, or in combination of two or more kinds thereof. Among these components, as the dicarboxylic acid component, asymmetric aromatic dicarboxylic acids (e.g., isophthalic acid, phthalic acid and 5-sodium sulfoisophthalic acid), aliphatic dicarboxylic acids ($C_{6-12}$ aliphatic dicarboxylic acids such as adipic acid), or the like are generally used. As the diol component, alkanediols (e.g., $C_{3-6}$ alkanediols such as 1,3-propanediol, 1,4-butanediol, 1,6-hexanediol and neopentyl glycol), polyoxyalkylene glycols (e.g., polyoxy-$C_{2-4}$ alkylene glycols such as diethylene glycol, triethylene glycol, polyethylene glycol and polytetramethylene glycol) or the like are generally used. Among them, asymmetric aromatic dicarboxylic acids such as isophthalic acid, and polyoxy-$C_{2-4}$ alkylene glycols such as diethylene glycol are preferable. The modified polyalkylene arylate-based resin (b) may be an elastomer having a $C_{2-4}$ alkylene arylate (e.g., ethylene terephthalate or butylene terephthalate) as a hard segment and a polyoxyalkylene glycol or the like as a soft segment.

In the modified polyalkylene arylate-based resin (b), a ratio of the dicarboxylic acid component (e.g., isophthalic acid) for reducing the melting point or softening point is, for example, 1 to 50 mol %, preferably 5 to 50 mol %, more preferably 15 to 40 mol % based on the whole amount of dicarboxylic acid components constituting the modified polyalkylene arylate-based resin (b). A ratio of the diol component (e.g., diethylene glycol) for reducing the melting point or softening point is, for example, less than or equal to 30 mol %, preferably less than or equal to 10 mol % (e.g., 0.1 to 10 mol %) based on the whole amount of diol components constituting the modified polyalkylene arylate-based resin (b). If the ratio of copolymerization components is to too low, sufficient crimps are not expressed, and thus the form stability and stretchability of the nonwoven fabric after expression of crimps are lowered. On the other hand, if the ratio of copolymerizable components is too high, although crimp expressing performance is improved, it is difficult to stably perform spinning.

The modified polyalkylene arylate-based resin (b) may include, as monomer components, polyvalent carboxylic acid components such as trimellitic acid and pyromellitic acid, polyol components such as glycerol, trimethylolpropane, trimethylolethane and pentaerythritol, and so on as necessary.

A transverse cross-sectional shape of the conjugated fiber (cross-sectional shape perpendicular to the longitudinal direction of the fiber) is not limited to a general solid cross-sectional shape such as a circular cross-sectional shape or an irregular cross-sectional shape [flat shape, elliptical shape, polygonal shape, 3 to 14-foliated shape, T-shape, H-shape, V-shape, dog-bone (I-shape) or the like], and it may be a hollow cross-sectional shape or the like. Usually, the transverse cross-sectional shape of the conjugated fiber is a circular cross-sectional shape.

Examples of the transverse cross-sectional structure of the conjugated fiber include phase structures formed of a plurality of resins, such as, for example, structures of core-sheath type, sea-island type, blend type, parallel type (side-by-side type or multilayer lamination type), radial type (radial lamination type), hollow radial type, block type, random composite type and the like. In particular, a structure in which phase parts neighbor each other (so-called bimetal structure), and a structure in which a phase structure is asymmetric, such as, for example, a structure of eccentric core-sheath type or parallel type are preferable because spontaneous crimps are easily expressed by heating.

In the case where the conjugated fiber has a structure of core-sheath type such as a structure of eccentric core-sheath type, the core part may be made from a thermal adhesive resin under moisture (e.g., a vinyl alcohol-based polymer such as an ethylene-vinyl alcohol copolymer or polyvinyl alcohol), or a thermoplastic resin having a low melting point or softening point (e.g., polystyrene or low-density polyethylene) as long as there is a difference in thermal shrinkage with the non thermal adhesive resin under moisture of the sheath part situated at the surface, and thus the fiber can be crimped.

The conjugated fibers have an average fineness of, for example, 0.1 to 50 dtex, and preferably 0.5 to 10 dtex, more preferably 1 to 5 dtex. If the fineness is too small, it is difficult to produce fibers themselves, and, in addition, it is difficult to secure fiber strength. Further, it is difficult to express fine coil-shaped crimps in a process of expressing crimps. On the other hand, if the fineness is too large, fibers are rigid, so that it is difficult to express sufficient crimps.

The conjugated fibers have an average fiber length of, for example, 10 to 100 mm, and preferably 20 to 80 mm, more preferably 25 to 75 mm. If the average fiber length is too short, it is difficult to form a fiber web, and, in addition, entanglement of crimped fibers is insufficient when crimps are expressed, so that it may be difficult to secure the strength and stretchability of the nonwoven fabric. If the average fiber length is too long, it is difficult to form a fiber web with a uniform basis weight, and further, a large number of entanglements of fibers are expressed at the time of forming the web, so that fibers may obstruct one another at the time of expressing crimps, resulting in difficulty in expression of stretchability. When the average fiber length is within the above range, some fibers crimped on the nonwoven fabric surface are appropriately exposed on the nonwoven fabric surface, so that the self-adhesiveness of the nonwoven fabric can be improved. The average fiber length within the above range is advantageous for obtaining good hand cut property.

The above-described conjugated fiber is a latently crimped fiber, and when the conjugated fibers are heat-treated, crimps are expressed (or appear), and thus the conjugated fibers are fibers having substantially coil-shaped (helical or spiral spring-shaped) three-dimensional crimps.

The number of crimps (number of mechanical crimps) before heating is, for example, 0 to 30 crimps/25 mm, preferably 1 to 25 crimps/25 mm, more preferably 5 to 20 crimps/25 mm. The number of crimps after heating is, for example, greater than or equal to 30 crimps/25 mm (for example 30 to 200 crimps/25 mm), and preferably 35 to 150 crimps/25 mm.

As described above, the crimped fibers constituting the nonwoven fabric have substantially coil-shaped crimps after expression of crimps. An average curvature radius of circles formed by the coils of the crimped fibers is, for example, 10 to 250 μm, and preferably 20 to 200 μm, more preferably 50 to 160 μm. The average curvature radius is an index expressing an average size of circles formed by the coils of crimped fibers, and in the case where this value is large, the formed coil has a loose shape, i.e., a shape having a small number of crimps. If the number of crimps is small, the number of entanglements of crimped fibers also decreases, and it is difficult to recover the shape against deformation of the coil shape, so that it is disadvantageous for expressing sufficient stretching performance. If the average curvature radius is too small, crimped fibers are not satisfactorily entangled with each other, so that it is difficult to secure web strength. Further, when the coil shape is deformed, stress is too large and breaking strength is excessively increased, so that it is difficult to obtain suitable stretchability.

In the crimped fibers, an average pitch (average crimp pitch) of the coil is, for example, 0.03 to 0.5 mm, preferably 0.03 to 0.3 mm, more preferably 0.05 to 0.2 mm. If the average pitch is excessively large, the number of coil crimps that can be expressed per fiber decreases, so that sufficient stretchability cannot be exhibited. If the average pitch is excessively small, crimped fibers are not satisfactorily entangled with each other, so that it becomes difficult to secure the strength of the nonwoven fabric.

The nonwoven fabric (fibrous web) may contain other fibers (non-conjugated fibers) in addition to the above-described conjugated fibers. Specific examples of the non-conjugated fiber include, in addition to fibers constituted of the above-described non thermal adhesive resin under moisture or thermal adhesive resin under moisture, fibers constituted of cellulose-based fibers [e.g., natural fibers (e.g., cotton, wool, silk, and hemp), semi-synthetic fibers (e.g., acetate fibers such as triacetate fibers), and regenerated fibers (e.g., rayon, polynosic, cupra, and lyocell (e.g., registered trademark "Tencel"))] and the like. An average fineness and average fiber length of the non-conjugated fibers can be the same as those of the conjugated fibers. The non-conjugated fibers may be used singly, or in combination of two or more kinds thereof.

A ratio (mass ratio) of the conjugated fiber and the non-conjugated fiber is preferably adjusted appropriately so that the stress relaxation rate of the fibrous sheet falls within the above-described range. As the ratio, the conjugated fiber/the non-conjugated fiber is, for example, 50/50 to 100/0, and preferably 60/40 to 100/0, more preferably 70/30 to 100/0, still more preferably 80/20 to 100/0, particularly preferably 90/10 to 100/0. A balance between the strength and stretchability or flexibility of the nonwoven fabric can be adjusted by blending the non-conjugated fibers.

The nonwoven fabric (fibrous web) may contain commonly used additives, such as stabilizers (e.g., thermal stabilizers, ultraviolet absorbers, light stabilizers, and antioxidants), antibacterial agents, deodorants, fragrances, colorants (dyes and pigments), fillers, antistatic agents, flame retardants, plasticizers, lubricants, and crystallization speed retardants. The additives may be used singly, or in combination of two or more kinds thereof. The additive may be supported to the fiber surface or may be contained in the fiber.

The fibrous sheet constituted of the nonwoven fabric containing the crimped fibers can be suitably produced by a method including a step (web formation step) of forming fibers containing the above-described conjugated fibers (latently crimped fibers) into a web and a step (heating step) of heating the fibrous web and crimping the conjugated fibers.

As a method of forming the fibrous web in the web formation step, it is possible to use a commonly used method such as a direct method including a spunbond method or a melt-blow method, a carding method using melt-blow fibers, staple fibers, or the like, or a dry method such as an air-lay method. Among them, a carding method using to melt-blow fibers or staple fibers, particularly, a carding method using staple fibers is commonly used. Examples of the web obtained by using staple fibers include a random web, a semi-random web, a parallel web, and a cross-wrap web.

Prior to the heating step, an entangling step of entangling at least some fibers in the fibrous web may be carried out. A nonwoven fabric in which crimped fibers are suitably entangled can be obtained in the next heating step by carrying out the entangling step. Although the entangling method may be a method of mechanically performing entanglement, preferred is a method of performing entanglement by spraying or injecting (blowing) water. The entanglement of the fibers with water flow is advantageous in increasing the density of the entanglement by crimping in the heating step. Although the water to be sprayed or injected may be blown from one or both sides of the fibrous web, it is preferable to blow water from both sides from the viewpoint of efficiently performing strong entanglement.

A jetting pressure of water in the entangling step is, for example, greater than or equal to 2 MPa, preferably 3 to 12 MPa, more preferably 4 to 10 MPa, so that the fiber entanglement falls within an appropriate range. A temperature of the sprayed or injected water is, for example, 5 to 50° C., and preferably 10 to 40° C.

As a method of spraying or injecting water, preferred is a method of injecting water with use a nozzle or the like having a regular spray area or spray pattern, from the viewpoint of convenience and the like. Specifically, water can be injected onto a fibrous web transferred by a belt conveyor such as an endless conveyor, while the fibrous web is placed on a conveyor belt. The conveyor belt may be water-permeable, and water may pass through the water-permeable conveyor belt from the back side of the fibrous web to be injected onto the fibrous web. In order to suppress scattering of fibers due to water injecting, the fibrous web may be wetted with a small amount of water in advance.

As the nozzle for spraying or injecting water, a plate or die having predetermined orifices successively arranged in a width direction thereof is used, and the plate or die may be disposed to arrange the orifices in the width direction of the fibrous web to be conveyed. The number of orifice lines may be at least one, and a plurality of orifice lines may be arranged in parallel. A plurality of nozzle dies each having one orifice line may be installed in parallel.

Prior to the entangling step, a step (uneven distribution step) of unevenly distributing the fibers in the fibrous web in the plane may be provided. When this step is carried out, a region where fiber density becomes sparse is formed in the fibrous web, and therefore, in the case where the entangling step is water flow entanglement, a water flow can be efficiently injected into the fibrous web, so that moderate entanglement can be easily realized not only on a surface of the fibrous web but also inside thereof.

The uneven distribution step can be performed by spraying or injecting low-pressure water onto the fibrous web. The low-pressure water may be successively sprayed or injected onto the fibrous web, but it is preferable that the low-pressure water is intermittently or periodically sprayed onto the fibrous web. When water is intermittently or periodically sprayed onto the fibrous web, it is possible to periodically and alternately form a plurality of low-density portions and a plurality of high-density portions.

It is desirable that a jetting pressure of water in the uneven distribution step is as low as possible, and the jetting pressure of water is, for example, 0.1 to 1.5 MPa, preferably 0.3 to 1.2 MPa, more preferably 0.6 to 1.0 MPa. A temperature of the sprayed or injected water is, for example, 5 to 50° C., and preferably 10 to 40° C.

As a method of spraying or injecting water intermittently or periodically, there is no particular limitation as long as it is a method capable of periodically and alternately forming a gradient of density on the fibrous web: however, from the viewpoint of convenience and the like, preferred is a method of injecting water through a plate-like object (e.g., porous plate) having a regular spray area or spray pattern formed with a plurality of holes.

In the heating step, the fibrous web is heated with high temperature steam and crimped. In the method of treating the fibrous web with high temperature steam, the fibrous web is exposed to a high temperature or superheated steam (high pressure steam) flow, whereby coil crimps occur in the conjugated fibers (latently crimped fibers). The fibrous web has air permeability. Accordingly, high temperature steam permeates into the fibrous web even in treatment from one direction, substantially uniform crimps are expressed in the thickness direction, and the fibers are uniformly entangled with each other.

The fibrous web shrinks simultaneously with high temperature steam treatment. Accordingly, it is desirable that the fibrous web to be supplied is overfed according to the area shrinkage ratio of an intended nonwoven fabric immediately before the fibrous web is exposed to high temperature steam. A ratio of the overfeeding is 110 to 300%, preferably 120 to 250%, based on the length of the intended nonwoven fabric.

In order to supply the fibrous web with steam, a commonly used steam injecting apparatus may be used. The steam injecting apparatus is preferably an apparatus capable of generally uniformly blowing steam over the whole width of the fibrous web with a desired pressure and amount. The steam injecting apparatus may be provided only on one surface side of the fibrous web, or in order to treat the front and back of the fibrous web with steam at a time, the steam spraying apparatus may be further provided on the other surface side.

Since the high temperature steam injected from the steam injecting apparatus is a gas flow, the high temperature steam enters inside the fibrous web without significantly moving the fibers in the fibrous web, unlike the water flow entanglement treatment and the needle punching treatment. By virtue of the entry action of the steam flow into the fibrous web, the steam flow efficiently covers a surface of each fiber existing in the fibrous web, and enables uniform thermal crimping. Since heat can be satisfactorily conducted inside the fibrous web, as compared with the dry heat treatment, the degree of crimping is almost uniform in the plane direction and the thickness direction.

Similarly to the nozzle for water flow entanglement, as a nozzle for injecting high temperature steam, a plate or die having predetermined orifices successively arranged in a width direction thereof is used, and the plate or die may be disposed to arrange the orifices in the width direction of the fibrous web to be conveyed. The number of orifice lines may be at least one, and a plurality of orifice lines may be arranged in parallel. A plurality of nozzle dies each having one orifice line may be installed in parallel.

A pressure of the high temperature steam to be used can be selected from the range of 0.1 to 2 MPa (for example, 0.2 to 1.5 MPa). If the pressure of the steam is too high, the fibers forming the fibrous web may move more than required to cause disturbance of the texture, or the fibers may be intermingled more than required. When the pressure is too weak, it becomes impossible to give the quantity of heat required for expression of crimps of the fibers to the fibrous web, or the steam cannot penetrate the fibrous web and expression of crimps of the fibers in the thickness direction tends to be nonuniform. Although depending on materials of the fibers and the like, a temperature of the high temperature steam can be selected from the range of 70 to 180° C. (for example, 80 to 150° C.). A treatment speed with high temperature steam can be selected from the range of less than or equal to 200 m/minute (for example, 0.1 to 100 m/minute).

After thus causing expression of crimps of the conjugated fiber in the fibrous web, there may be a case where water remains in the nonwoven fabric, and therefore, a drying step of drying the nonwoven may be provided as necessary. Examples of the drying method may include a method using a drying apparatus such as a cylinder dryer or a tenter; a non-contact method such as far infrared ray irradiation, microwave irradiation, or electron beam irradiation; a method of blowing hot air or passing the nonwoven fabric through hot air, and the like.

Examples of a method of adjusting the stress relaxation rate to the above-described range in the method of producing a fibrous sheet as described above may include a method of adjusting a content ratio of the conjugated fibers and the non-conjugated fibers; a method of adjusting conditions of the high temperature steam (in particular, temperature and/or pressure) used in the heating step; a method of adjusting the drying temperature in the drying step; and the like.

Second Embodiment (1) Characteristics of Fibrous Sheet

A fibrous sheet according to the present embodiment (hereinafter also simply referred to as the "fibrous sheet") is a fibrous sheet capable of being suitably used not only as a general bandage but also as a medical article such as a compression bandage used for hemostasis, compression therapy, and so on. When a thickness of a single fibrous sheet measured in accordance with A method specified in JIS L 1913 (load: 0.5 kPa) is defined as $T_1$ [mm], and a thickness of three superimposed sheets measured under the same conditions is defined as $T_3$ [mm], the fibrous sheet satisfies the following formula [A]:

$$\{T_3(3\times T_1)\}\times 100 \leq 85 [\%] \qquad [A].$$

The fibrous sheet satisfying the above formula [A] is less liable to disturb the bending motion of a site to be bent and stretched, such as a joint part, even if the fibrous sheet is wrapped around the site. When this site is for example a small joint part of a finger or the like, difficulty in moving the site is remarkable when the fibrous sheet is wrapped around the site. However, according to the fibrous sheet satisfying the above formula [A], it is possible to effectively prevent the bending motion from being disturbed, even when the fibrous sheet is wrapped around such a small joint part. From the viewpoint of ease of bending of a site to be bent and stretched when the fibrous sheet is wrapped around the site, the left side of the above formula [A] is preferably less than or equal to 84%, more preferably less than or equal to 83%. The left side of the above formula [A] is usually greater than or equal to 50%, more typically greater than or equal to 60%.

As another means for suppressing the disturbance of the bending motion, it is conceivable to reduce a basis weight of the fibrous sheet. However, if the basis weight is reduced, the strength of the fibrous sheet decreases, and for example, the abrasion resistance of an outer exposed portion is reduced when the fibrous sheet is wrapped around an application site, or the fibrous sheet tends to be broken when extended; thus, it becomes difficult to obtain sufficient durability. On the other hand, according to the fibrous sheet satisfying the above formula [A], it is possible to suppress the disturbance of the bending motion regardless of the basis weight adjustment. Accordingly, the invention according to the present embodiment can also provide a fibrous sheet capable of suppressing the disturbance of the bending motion and having good durability.

From the viewpoint of ease of bending of a site to be bent and stretched when the fibrous sheet is wrapped around the site, the fibrous sheet preferably has extensibility. As described above, in the present specification, "extensible/ having extensibility" means that a stress at 50% extension is exhibited in at least one direction (first direction) in the sheet plane. The stress at 50% extension is a stress at extension at the time of extension at 50% elongation (immediately after extension) and is measured by a tensile test in accordance with the "Test methods for nonwovens" specified in JIS L 1913.

When the fibrous sheet is a bandage having, for example, a length direction and a width direction and it is assumed that the bandage is wrapped around a joint part of a finger or the like, the bandage is generally wrapped such that its width direction and the length direction of the finger are parallel or approximately parallel to each other. In this case, in order to improve ease of bending of the finger joint part, it is preferable that the bandage has good extensibility at least in the width direction. From such a viewpoint, when the fibrous sheet has, for example, a length direction and a width direction like a bandage, the first direction is preferably the width direction of the fibrous sheet. This width direction may be a direction orthogonal to a flow direction (MD direction) of the fibrous sheet in a production process, that is, a CD direction.

As described above, the fibrous sheet is excellent in extensibility preferably in at least one direction (first direction) in the sheet plane, more preferably in the width direction. More specifically, when a stress at extension at the time of extension in the first direction at 50% elongation is defined as stress $S_1$ (N/50 mm) at 50% extension, and a stress at extension at the time of extension in a second direction orthogonal to the first direction in a plane at 50% elongation is defined as stress $S_2$ (N/50 mm) at 50% extension, the fibrous sheet satisfies the following formula [B]:

$$S_2/S_1 \geq 3 \qquad [B].$$

The left side of the above formula [B] is preferably greater than or equal to 5. The left side of the above formula [B] is usually less than or equal to 20. According to the fibrous sheet having the first direction and satisfying the above formula [B], the disturbance of the bending motion can be more effectively suppressed in a use form in which the fibrous sheet is wrapped such that the first direction of the fibrous sheet and, for example, the length direction of the finger are parallel or approximately parallel to each other. The left side of the above formula [B] is preferably less than or equal to 10 from the viewpoint of imparting relatively good extensibility also in the second direction.

The stress $S_1$ at 50% extension in the first direction is preferably 0.1 to 20 N/50 mm, more preferably 0.5 to 15 N/50 mm, further preferably 1 to 12 N/50 mm.

When the fibrous sheet has a length direction and a width direction, the second direction orthogonal to the first direction in the plane is preferably the length direction. The length direction may be a flow direction (MD direction) of the fibrous sheet in a production process. The stress $S_2$ at 50% extension in the second direction and a stress at 50% extension in a direction other than the first direction are each preferably 0.5 to 60 N/50 mm, more preferably 1 to 45 N/50 mm, still more preferably 2 to 40 N/50 mm.

The fibrous sheet preferably exhibits self-adhesiveness. As described above, in the present specification, the "self-adhesiveness" refers to a property allowing fibers on a fibrous sheet surface to engage with each other or come into close contact with each other due to superposition (contact) of the fibers and to be hooked or fixed. The fibrous sheet having self-adhesiveness is advantageous when the fibrous sheet is a bandage or the like. For example, in the case where the fibrous sheet is a bandage, after the bandage is wrapped around an application site, the wrapped fibrous sheets are pressed against each other while being extended by such an operation that an end of the bandage is overlapped on (or torn and then overlapped on) a bandage surface located to under the end, so that the fibrous sheets are joined and fixed to each other, thereby expressing self-adhesiveness.

When the fibrous sheet itself has self-adhesiveness, it is unnecessary to form a layer formed of a self-adhesive agent such as an elastomer or a pressure-sensitive adhesive on a surface of the fibrous sheet or to prepare separately a fastener for fixing the tip after wrapping. For example, Japanese Patent Laying-Open No. 2005-095381 (PTD 4) describes that an acrylic polymer (claim 1) or a latex (paragraphs [0004] to [0006]) is caused to adhere as a self-adhesive agent to at least one side of a bandage base material. Formation of a layer formed of an elastomer such as latex on the fibrous sheet surface is effective for enhancing self-adhesiveness.

However, it is preferable that the fibrous sheet according to the present embodiment is constituted only of a nonelastomer material. More specifically, it is preferable that the fibrous sheet is constituted only of fibers. When such a layer formed of an elastomer is formed on the fibrous sheet surface, gaps on the fibrous sheet surface are sealed with the elastomer, so that when the fibrous sheets are stacked on each other, it is difficult for fibers to mesh with each other. Therefore, the thickness $T_3$ of three superimposed fibrous sheets is not satisfactorily reduced, and as a result, it tends to be relatively difficult to satisfy the above formula [A]. The layer formed of an elastomer may induce skin irritation and allergy when wrapped around an application site.

The self-adhesiveness of the fibrous sheet can be evaluated by a curved surface sliding stress. From the viewpoint of the self-adhesiveness, it is preferable that the fibrous sheet has a curved surface sliding stress of, for example, greater than or equal to 3 N/50 mm, preferably greater than or equal to 5 N/50 mm, and the curved surface sliding stress is preferably higher than breaking strength. Since it is relatively easy to unwrap the wrapped fibrous sheet if desired, the curved surface sliding stress is preferably less than or equal to 30 N/50 mm, more preferably less than or equal to 25 N/50 mm. The curved surface sliding stress is measured using a tensile tester in accordance with the method described in Examples section (FIGS. 1 to 3).

The fibrous sheet preferably has a hand cut property. As described above, in the present specification, the "hand cut property" refers to a property enabling breakage (cutting) by hand tension. The hand cut property of the fibrous sheet can be evaluated by breaking strength. From the viewpoint of the hand cut property, the fibrous sheet has a breaking strength in at least one direction in the sheet plane of preferably 5 to 100 N/50 mm, more preferably 8 to 60 N/50 mm, further preferably 10 to 40 N/50 mm. When the breaking strength is within the above range, it is possible to impart a good hand cut property enabling relatively easy breakage (cutting) by hand. If the breaking strength is too large, the hand cut property deteriorates, making it difficult to cut the fibrous sheet with one hand, for example. On the other hand, if the breaking strength is too small, the strength of the fibrous sheet becomes insufficient to cause easy breakage of the fibrous sheet, and durability and handleability are lowered. The breaking strength is measured by a tensile test in accordance with the "Test methods for nonwovens" specified in JIS L 1913.

At least one direction in the sheet plane is a tensile direction when the fibrous sheet is cut by hand, and is preferably the above-described second direction. The second direction may be the MD direction, and when the fibrous sheet has, for example, a length direction and a width direction like a bandage, the first direction is preferably the length direction of the fibrous sheet. That is, when the fibrous sheet is used as a bandage, it is usual to break the bandage in the length direction after the bandage is wrapped around an application site while being extended along the length direction thereof, and therefore the second direction is preferably the length direction as the tensile direction.

The breaking strength in a direction other than at least one direction in the sheet plane, for example, the first direction (such as the CD direction), or a width direction when the fibrous sheet has a length direction and the width direction like a bandage is, for example, 0.1 to 300 N/50 mm, preferably 0.5 to 100 N/50 mm, more preferably 1 to 20 N/50 mm.

From the viewpoint of the hand cut property, it is preferable that the fibrous sheet is constituted only of a nonelastomer material. More specifically, it is preferable that the fibrous sheet is constituted only of fibers. If a layer formed of an elastomer, etc. is formed on the fibrous sheet surface, the hand cut property may be lowered.

The fibrous sheet has an elongation at break in at least one direction in the sheet plane of, for example, greater than or equal to 50%, preferably greater than or equal to 60%/o, more preferably greater than or equal to 80%. When the elongation at break is within the above range, it is advantageous for enhancing the stretchability of the fibrous sheet. The elongation at break in at least one direction in the sheet plane is usually less than or equal to 300% and preferably less than or equal to 250%. The elongation $2o$ at break is also measured by a tensile test in accordance with the "Test methods for nonwovens" specified in JIS L 1913.

From the viewpoint of ease of bending of a site to be bent and stretched, such as a joint part, when the fibrous sheet is wrapped around the site, at least one direction in the sheet plane is preferably the above-described first direction. The first direction may be the CD direction, and when the fibrous sheet has, for example, a length direction and a width direction like a bandage, the first direction is preferably the width direction of the fibrous sheet.

The elongation at break in a direction other than at least one direction in the sheet plane, for example, the second direction (such as the MD direction), or a length direction when the fibrous sheet has the length direction and a width direction like a bandage is, for example, 10 to 500%, preferably 100 to 350%.

The fibrous sheet has a recovery rate after 50% extension in at least one direction in the sheet plane (recovery rate after 50% extension) is preferably greater than or equal to 70% (less than or equal to 100%), more preferably greater than or equal to 80%, further preferably greater than or equal to 90%. When the recovery rate after 50% extension is within the range, the followability to extension is enhanced, and for example when the fibrous sheet is wrapped around a site to be bent and stretched, such as a joint part, the fibrous sheet satisfactorily follows the bending motion and shape of the site, and at the same time, it is advantageous for improvement of the self-adhesiveness due to friction between the overlapped fibrous sheets. If the extension recovery rate is excessively small, the fibrous sheet cannot follow the bending motion of the site, and deformation of the fibrous sheet caused by this motion does not return to its original shape, thus weakening fixation of the wrapped fibrous sheet.

At least one direction in the sheet plane is preferably the above-described first direction where the followability to the bending motion of a site to be bent and stretched, such as a joint part, is particularly required when the fibrous sheet is wrapped around the site. The first direction may be the CD direction, and when the fibrous sheet has, for example, a length direction and a width direction like a bandage, the first direction is preferably the width direction of the fibrous sheet.

The recovery rate after 50% extension is defined by the following formula:

Recovery rate after 50% extension (%)=100−X when, in a tensile test in accordance with the "Test methods for nonwovens" specified in JIS L 1913, a residual strain (%) after the test is defined as X when load is removed immediately after the elongation rate reaches 50%.

The recovery rate after 50% extension in a direction other than at least one direction in the sheet plane, for example, the second direction (such as the MD direction), or a length direction when the fibrous sheet has the length direction and a width direction like a bandage is, for example, greater than or equal to 70% (less than or equal to 100%), preferably greater than or equal to 80%.

The fibrous sheet has a compression elastic modulus Pe of preferably less than or equal to 85%, more preferably less than or equal to 80%. It is advantageous for satisfying the above formula [A] that the compression elastic modulus Pe is within this range, and consequently it is advantageous in achieving a fibrous sheet less likely to disturb the bending motion of a joint part or the like. A lower limit of the compression elastic modulus Pe is not particularly limited, and is, for example, 50%. The compression elastic modulus Pe is calculated in accordance with the "Test methods for nonwovens" specified in JIS L 1913 by the following formula [C]:

$$Pe=\{(T_1'-T)/(T_1-T)\}\times 100 \qquad [C].$$

$T_1$ is the thickness [mm] when an initial load (0.5 kPa) is applied, and has the same meaning as $T_1$ in the above formula [A]. T is the thickness [mm] when a load of 30 kPa is applied. $T_1'$ is the thickness [mm] when the initial load is restored.

The fibrous sheet has a basis weight of preferably 30 to 300 g/m², more preferably 50 to 200 g/m². From the viewpoint of more effectively suppressing the disturbance of the bending motion, the basis weight is more preferably less than or equal to 180 g/m². According to the fibrous sheet of the present embodiment, even when the basis weight is large (for example, greater than or equal to 50 g/m², greater than or equal to 70 g/m², greater than or equal to 90 g/m², greater than or equal to 110 g/m², further greater than or equal to 130 g/m²), it is possible to effectively suppress the disturbance of the bending motion of a joint part or the like.

The thickness $T_1$ of the fibrous sheet (the thickness $T_1$ has the same meaning as $T_1$ in the above formula [A]) is, for example, 0.2 to 5 mm, preferably 0.3 to 3 mm, more preferably 0.4 to 2 mm. When the basis weight and the thickness are within these ranges, a balance among the ease of bending exhibited when wrapping the fibrous sheet, the extensibility, and the flexibility, touch feeling and cushioning property of the fibrous sheet is good. A density (bulk density) of the fibrous sheet can be a value corresponding to the above-described basis weight and thickness, and the density (bulk density) is, for example, 0.03 to 0.5 g/cm³, preferably 0.04 to 0.4 g/cm³, more preferably 0.05 to 0.2 g/cm³. From the viewpoint of more effectively suppressing the disturbance of the bending motion, the density is more preferably less than or equal to 0.15 g/cm³.

In the fibrous sheet, a difference ΔT between the thickness $T_1$ when the initial load (0.5 kPa) is applied and the thickness T when a load of 30 kPa is applied is preferably greater than or equal to 0.05 mm, more preferably greater than or equal to 0.1 mm. It is advantageous for satisfying the above formula [A] that the thickness difference ΔT is in this range, and consequently it is advantageous in achieving a fibrous sheet less likely to disturb the bending motion of a joint part or the like. The thickness difference ΔT corresponds to ($T_1$-T) in the above formula [C]. An upper limit of the thickness difference ΔT is not particularly limited, and is, for example, 0.8 mm.

The fibrous sheet has an air permeability measured by the Frazier method of preferably greater than or equal to 0.1 cm³/(cm²·second), more preferably 1 to 500 cm³/(cm²·second), further preferably 5 to 300 cm³/(cm²·second), particularly preferably 10 to 200 cm³/(cm²-second). When the air permeability is within this range, the fibrous sheet is more suitably used for the human body, such as a bandage, because the fibrous sheet is good in air permeability and is hardly stuffy.

(2) Structure and Production Method of Fibrous Sheet

The fibrous sheet of the present embodiment is not particularly limited as long as it is constituted of fibers, and the fibrous sheet may be, for example, a woven fabric, a nonwoven fabric, a knit (knitted fabric), or the like. Although the shape of the fibrous sheet can be selected according to use application, it is preferably a rectangular sheet shape having a length direction and a width direction such as a tape shape or a belt shape (long shape). The fibrous sheet may have a single layer structure or a multilayer structure including two or more fibrous layers.

Examples of means for imparting stretchability and extensibility to the fibrous sheet may include 1) a method of subjecting a fibrous sheet substrate such as a woven fabric, a nonwoven fabric, or a knit to gathering; 2) a method of weaving, into a fibrous sheet, yarn formed of a stretchable material such as an elastomer typified by rubber; 3) a method of combining a layer formed of a stretchable material such as an elastomer with a nonstretchable fibrous sheet substrate or impregnating a nonstretchable fibrous sheet substrate with a stretchable material; 4) a method using crimped fibers crimped into a coil shape as at least some fibers constituting a nonwoven fabric; and the like.

Among the above methods, the fibrous sheet according to the present embodiment is preferably obtained by using the method described in 4). Although the gathering described in 1) is effective in that stretchability can be effectively imparted to the fibrous sheet, it is relatively difficult to obtain a fibrous sheet satisfying the above formula [A] depending on the wavy shape of the gather. According to the method 2), stretchability can be easily imparted to the fibrous sheet; however, since a rubber yarn or the like is woven, there is a fear that ease of bending exhibited when wrapping the fibrous sheet may be deteriorated. As described above, the method 3) tends to make it relatively difficult to satisfy the above formula [A] by sealing the fibrous sheet surface with the elastomer.

From the viewpoint of ease of bending of a joint part exhibited when the fibrous sheet is wrapped around the joint part, self-adhesiveness, hand cut property, conformity (fitting property) with a concavo-convex site such as a joint exhibited when the fibrous sheet is wrapped around the concavo-convex site, etc., the fibrous sheet is preferably constituted of a nonwoven fabric, namely, the fibrous sheet is preferably a nonwoven fabric sheet. More preferably, the fibrous sheet is constituted of a nonwoven fabric containing crimped fibers crimped into a coil shape, and still more preferably, the fibrous sheet is constituted of a nonwoven fabric that contains the crimped fibers and that is not subjected to at least one of treatments (desirably all treatments) described in 1) to 3). Particularly preferably, the nonwoven fabric sheet is constituted only of the crimped fibers.

It is preferable that the fibrous sheet constituted of the nonwoven fabric containing the crimped fibers has a structure in which the respective fibers constituting this nonwoven fabric are not substantially fusion-bonded, but mainly the crimped fibers are entangled with each other at their crimped coil portions and bound or hooked. Further, it is preferable that most (the majority of) crimped fibers (axial direction of crimped fibers) are oriented substantially parallel to a sheet surface. As described above, in the present specification, "oriented substantially parallel to a surface direction" means a state where a portion in which a large number of crimped fibers (axial direction of crimped fibers) are locally oriented along a thickness direction is not repeatedly present, as in for example entanglement by needle punching.

In the fibrous sheet constituted of the nonwoven fabric containing the crimped fibers, the crimped fibers are preferably oriented in a certain direction in the sheet plane (for example, in the above-described second direction, preferably in the length direction), and the adjacent or intersecting crimped fibers are entangled with each other at their crimped coil portions. Even in the thickness direction (or oblique direction) of the fibrous sheet, the crimped fibers are preferably slightly entangled with each other. The entanglement of the crimped fibers can be caused by the process of shrinking a fibrous web as a precursor of the fibrous sheet.

The nonwoven fabric in which crimped fibers (axial direction of crimped fibers) are oriented in a certain direction in the sheet plane and entangled exhibits good stretchability (including extensibility) in this direction. In the case where the certain direction is, for example, the length direction, when a tensile force is applied to the stretchable nonwoven fabric in the length direction, the entangled crimped coil portion tends to extend and return to the original coil shape, so that high stretchability can be exhibited in the length direction. This stretchable nonwoven fabric can exhibit excellent extensibility in a direction (for example, the width direction) orthogonal to the certain direction in the sheet plane. The cushioning property and flexibility in the thickness direction can be expressed by slight entanglement of the crimped fibers in the thickness direction of the nonwoven fabric, whereby the nonwoven fabric can have good touch feeling and texture. The crimped coil portion easily entangles with another crimped coil portion by contact with a certain degree of pressure. The self-adhesiveness can be expressed by the entanglement of the crimped coil portions.

In the fibrous sheet constituted of the nonwoven fabric containing the crimped fibers, when a tensile force is applied to the orientation direction of the crimped fiber (for example, in the above-described second direction, preferably in the length direction), the entangled crimped coil portion extends due to elastic deformation, and when the tensile force is further applied, the fibrous sheet is finally unwrapped, so that the cutting property (hand cut property) is also good.

As described above, the nonwoven fabric capable of constituting the fibrous sheet preferably contains crimped fibers crimped into a coil shape. The crimped fiber is preferably oriented mainly in the surface direction of the nonwoven fabric, and further preferably crimps substantially evenly in the thickness direction. The crimped fiber can be constituted of a conjugated fiber in which a plurality of resins having different thermal shrinkage factors (or thermal expansion coefficients) form a phase structure.

The conjugated fiber constituting the crimped fiber is a fiber (latently crimped fiber) having an asymmetric or layered (so-called bimetal) structure crimped by heating due to a difference in thermal shrinkage factor (or thermal expansion coefficient) of a plurality of resins. The plurality of resins usually have mutually different softening points or melting points. The plurality of resins can be selected from thermoplastic resins such as, for example, polyolefin-based resins (e.g., poly-$C_{2-4}$ olefin-based resins such as low-density, medium-density or high-density polyethylene and polypropylene); acrylic resins (e.g., acrylonitrile-based resins having an acrylonitrile unit, such as acrylonitrile-vinyl chloride copolymers): polyvinyl acetal-based resins (e.g., polyvinyl acetal resins); polyvinyl chloride-based resins (e.g., polyvinyl chloride, vinyl chloride-vinyl acetate copolymers and vinyl chloride-acrylonitrile copolymers); polyvinylidene chloride-based resins (e.g., vinylidene chloride-vinyl chloride copolymers and vinylidene chloride-vinyl acetate copolymers); styrene-based resins (e.g., heat-resistant polystyrene); polyester-based resins (e.g., poly-$C_{2-4}$ alkylene arylate-based resins such as polyethylene terephthalate resins, polytrimethylene terephthalate resins, polybutylene terephthalate resins and polyethylene naphthalate resins); polyamide-based resins (e.g., aliphatic polyamide-based resins such as polyamide 6, polyamide 66, polyamide 11, polyamide 12, polyamide 610 and polyamide 612, semi-aromatic polyamide-based resins, and aromatic polyamide-based resins such as polyphenylene isophthalamide, polyhexamethylene terephthalamide and poly-p-phenylene-terephthalamide); polycarbonate-based resins (e.g., bisphenol A-type polycarbonate); polyparaphenylene benzobisoxazole resins; polyphenylene sulfide resins; polyurethane-based resins; and cellulose-based resins (e.g., cellulose esters). These thermoplastic resins may contain other copolymerizable units.

Among the thermoplastic resins, non thermal adhesive resins under moisture (or heat-resistant hydrophobic resins or nonaqueous resins) having a softening point or melting point greater than or equal to 100° C., such as, for example, polypropylene-based resins, polyester-based resins and polyamide-based resins are preferable because fibers are not melted or softened to be fused even when subjected to a heating treatment with high-temperature steam. Particularly, aromatic polyester-based resins and polyamide-based resins are preferable because they are excellent in balance among heat resistance, fiber formability, and so on. A resin exposed to surfaces of conjugated fibers constituting a nonwoven fabric (latently crimped fiber) is preferably at least a non thermal adhesive resin under moisture so that the conjugated fibers are not fused even when treated with high-temperature steam.

The plurality of resins forming the conjugated fiber may have different thermal shrinkage factors, and may be a combination of resins of the same kind, or a combination of different kinds of resins.

Preferably, the plurality of resins forming the conjugated fiber are a combination of resins of the same kind from the viewpoint of adhesiveness. In the case of the combination of resins of the same kind, usually a combination of a component (A) forming a homopolymer (essential component) and a component (B) forming a modification polymer (copolymer) is used. That is, for example, a copolymerizable monomer for reducing the crystallization degree, the melting point, the softening point, or the like is copolymerized with the homopolymer as an essential component to perform modification, whereby the crystallization degree may be reduced as compared to the homopolymer, or the polymer may be made noncrystalline to reduce the melting point or softening point as compared to the homopolymer. When the crystallization degree, the melting point, or the softening point is changed as described above, this can cause a difference in thermal shrinkage factor. The difference in melting point or softening point is, for example, 5 to 150° C., and preferably 40 to 130° C., more preferably 60 to 120° C. A ratio of the copolymerizable monomer to be used for modification is, for example, 1 to 50 mol %, preferably 2 to 40 mol %, more preferably 3 to 30 mol % (particularly 5 to 20 mol %) based on the whole amount of monomers. While a mass ratio between the component forming a homopolymer and the component forming a modification polymer can be selected according to the structure of fibers, the homopolymer component (A)/the modification polymer component (B) is for example 90/10 to 10/90, and preferably 70/30 to 30/70, more preferably 60/40 to 40/60.

The conjugated fiber is preferably a combination of aromatic polyester-based resins, more preferably a combination of a polyalkylene arylate-based resin (a) and a modified polyalkylene arylate-based resin (b) because latently crimpable conjugated fibers are easily produced. The polyalkylene arylate-based resin (a) can be a homopolymer of an aromatic dicarboxylic acid (e.g., a symmetric aromatic dicarboxylic acid such as terephthalic acid or naphthalene-2,6-dicarboxylic acid) and an alkanediol component (e.g., $C_{2-6}$ alkanediol such as ethylene glycol or butylene glycol). Specifically, a poly-$C_{2-4}$ alkylene terephthalate-based resin such as polyethylene terephthalate (PET) or polybutylene terephthalate (PBT), or the like is used, and usually, PET for use in general PET fibers having an intrinsic viscosity of 0.6 to 0.7 is used.

On the other hand, in the modified polyalkylene arylate-based resin (b), examples of a copolymerization component for reducing the melting point or softening point and the crystallization degree of the polyalkylene arylate-based resin (a) as an essential component include dicarboxylic acid components such as an asymmetric aromatic dicarboxylic acid, an alicyclic dicarboxylic acid and an aliphatic dicarboxylic acid; an alkanediol component having a chain length longer than that of alkanediol of the polyalkylene arylate-based resin (a); and/or an ether bond-containing diol component. The copolymerization components may be used singly, or in combination of two or more kinds thereof. Among these components, as the dicarboxylic acid component, asymmetric aromatic dicarboxylic acids (e.g., isophthalic acid, phthalic acid and 5-sodium sulfoisophthalic acid), aliphatic dicarboxylic acids ($C_{6-12}$ aliphatic dicarboxylic acids such as adipic acid), or the like are generally used. As the diol component, alkanediols (e.g., $C_{3-6}$ alkanediols such as 1,3-propanediol, 1,4-butanediol, 1,6-hexanediol and neopentyl glycol), polyoxyalkylene glycols (e.g., polyoxy-$C_{2-4}$ alkylene glycols such as diethylene glycol, triethylene glycol, polyethylene glycol and polytetramethylene glycol) or the like are generally used. Among them, asymmetric aromatic dicarboxylic acids such as isophthalic acid, and polyoxy-$C_{2-4}$ alkylene glycols such as diethylene glycol are preferable. The modified polyalkylene arylate-based resin (b) may be an elastomer having a $C_{2-4}$ alkylene arylate (e.g., ethylene terephthalate or butylene terephthalate) as a hard segment and a polyoxyalkylene glycol or the like as a soft segment.

In the modified polyalkylene arylate-based resin (b), a ratio of the dicarboxylic acid component (e.g., isophthalic acid) for reducing the melting point or softening point is, for example, 1 to 50 mol %, preferably 5 to 50 mol %, more preferably 15 to 40 mol % based on the whole amount of dicarboxylic acid components constituting the modified polyalkylene arylate-based resin (b). A ratio of the diol component (e.g., diethylene glycol) for reducing the melting point or softening point is, for example, less than or equal to 30 mol %, preferably less than or equal to 10 mol % (e.g., 0.1 to 10 mol %) based on the whole amount of diol components constituting the modified polyalkylene arylate-based resin (b). If the ratio of copolymerization components is too low, sufficient crimps are not expressed, and thus the form stability and stretchability of the nonwoven fabric after expression of crimps are lowered. On the other hand, if the ratio of copolymerizable components is too high, although crimp expressing performance is improved, it is difficult to stably perform spinning.

The modified polyalkylene arylate-based resin (b) may include, as monomer components, polyvalent carboxylic acid components such as trimellitic acid and pyromellitic acid, polyol components such as glycerol, trimethylolpropane, trimethylolethane and pentaerythritol, and so on as necessary.

A transverse cross-sectional shape of the conjugated fiber (cross-sectional shape perpendicular to the longitudinal direction of the fiber) is not limited to a general solid cross-sectional shape such as a circular cross-sectional shape or an irregular cross-sectional shape [flat shape, elliptical shape, polygonal shape, 3 to 14-foliated shape, T-shape, H-shape, V-shape, dog-bone (I-shape) or the like], and it may be a hollow cross-sectional shape or the like. Usually, the transverse cross-sectional shape of the conjugated fiber is a circular cross-sectional shape.

Examples of the transverse cross-sectional structure of the conjugated fiber include phase structures formed of a plurality of resins, such as, for example, structures of core-sheath type, sea-island type, blend type, parallel type (side-by-side type or multilayer lamination type), radial type (radial lamination type), hollow radial type, block type, random composite type and the like. In particular, a structure in which phase parts neighbor each other (so-called bimetal structure), and a structure in which a phase structure is asymmetric, such as, for example, a structure of eccentric core-sheath type or parallel type are preferable because spontaneous crimps are easily expressed by heating.

In the case where the conjugated fiber has a structure of core-sheath type such as a structure of eccentric core-sheath type, the core part may be made from a thermal adhesive resin under moisture (e.g., a vinyl alcohol-based polymer such as an ethylene-vinyl alcohol copolymer or polyvinyl alcohol), or a thermoplastic resin having a low melting point or softening point (e.g., polystyrene or low-density polyethylene) as long as there is a difference in thermal shrinkage with the non thermal adhesive resin under moisture of the sheath part situated at the surface, and thus the fiber can be crimped.

The conjugated fibers have an average fineness of, for example, 0.1 to 50 dtex, and preferably 0.5 to 10 dtex, more preferably 1 to 5 dtex. If the fineness is too small, it is difficult to produce fibers themselves, and, in addition, it is difficult to secure fiber strength. Further, it is difficult to express fine coil-shaped crimps in a process of expressing crimps. On the other hand, if the fineness is too large, fibers are rigid, so that it is difficult to express sufficient crimps.

The conjugated fibers have an average fiber length of, for example, 10 to 100 mm, and preferably 20 to 80 mm, more preferably 25 to 75 mm. If the average fiber length is too short, it is difficult to form a fiber web, and, in addition, entanglement of crimped fibers is insufficient when crimps are expressed, so that it may be difficult to secure the strength and stretchability of the nonwoven fabric. If the average fiber length is too long, it is difficult to form a fiber web with a uniform basis weight, and further, a large number of entanglements of fibers are expressed at the time of forming the web, so that fibers may obstruct one another at the time of expressing crimps, resulting in difficulty in expression of stretchability. When the average fiber length is within the above range, some fibers crimped on the nonwoven fabric surface are appropriately exposed on the nonwoven fabric surface, so that the self-adhesiveness of the nonwoven fabric can be improved. The average fiber length within the above range is advantageous for obtaining good hand cut property.

The above-described conjugated fiber is a latently crimped fiber, and when the conjugated fibers are heat-treated, crimps are expressed (or appear), and thus the conjugated fibers are fibers having substantially coil-shaped (helical or spiral spring-shaped) three-dimensional crimps.

The number of crimps (number of mechanical crimps) before heating is, for example, 0 to 30 crimps/25 mm, preferably 1 to 25 crimps/25 mm, more preferably 5 to 20 crimps/25 mm. The number of crimps after heating is, for example, greater than or equal to 30 crimps/25 mm (for example 30 to 200 crimps/25 mm), and preferably 35 to 150 crimps/25 mm.

As described above, the crimped fibers constituting the nonwoven fabric have substantially coil-shaped crimps after expression of crimps. An average curvature radius of circles formed by the coils of the crimped fibers is, for example, 10 to 250 μm, and preferably 20 to 200 μm, more preferably 50 to 160 μm. The average curvature radius is an index expressing an average size of circles formed by the coils of crimped fibers, and in the case where this value is large, the formed coil has a loose shape, i.e., a shape having a small number of crimps. If the number of crimps is small, the number of entanglements of crimped fibers also decreases, and it is difficult to recover the shape against deformation of the coil shape, so that it is disadvantageous for expressing sufficient stretching performance. If the average curvature radius is too small, crimped fibers are not satisfactorily entangled with each other, so that it is difficult to secure web strength. Further, when the coil shape is deformed, stress is too large and breaking strength is excessively increased, so that it is difficult to obtain suitable stretchability.

In the crimped fibers, an average pitch (average crimp pitch) of the coil is, for example, 0.03 to 0.5 mm, preferably 0.03 to 0.3 mm, more preferably 0.05 to 0.2 mm. If the average pitch is excessively large, the number of coil crimps that can be expressed per fiber decreases, so that sufficient stretchability cannot be exhibited. If the average pitch is excessively small, crimped fibers are not satisfactorily entangled with each other, so that it becomes difficult to secure the strength of the nonwoven fabric.

The nonwoven fabric (fibrous web) may contain other fibers (non-conjugated fibers) in addition to the above-described conjugated fibers. Specific examples of the non-conjugated fiber include, in addition to fibers constituted of the above-described non thermal adhesive resin under moisture or thermal adhesive resin under moisture, fibers constituted of cellulose-based fibers [e.g., natural fibers (e.g., cotton, wool, silk, and hemp), semi-synthetic fibers (e.g., acetate fibers such as triacetate fibers), and regenerated fibers (e.g., rayon, polynosic, cupra, and lyocell (e.g., registered trademark "Tencel"))] and the like. An average fineness and average fiber length of the non-conjugated fibers can be the same as those of the conjugated fibers. The non-conjugated fibers may be used singly, or in combination of two or more kinds thereof.

A ratio (mass ratio) of the conjugated fiber and the non-conjugated fiber is preferably adjusted appropriately so that the fibrous sheet satisfies the above formula [A]. As the ratio, the conjugated fiber/the non-conjugated fiber is, for example, 50/50 to 100/0, and preferably 60/40 to 100/0, more preferably 70/30 to 100/0, still more preferably 80/20 to 100/0, particularly preferably 90/10 to 100/0. A balance between the strength and stretchability or flexibility of the nonwoven fabric can be adjusted by blending the non-conjugated fibers.

The nonwoven fabric (fibrous web) may contain commonly used additives, such as stabilizers (e.g., thermal stabilizers, ultraviolet absorbers, light stabilizers, and antioxidants), antibacterial agents, deodorants, fragrances, colorants (dyes and pigments), fillers, antistatic agents, flame retardants, plasticizers, lubricants, and crystallization speed retardants. The additives may be used singly, or in combination of two or more kinds thereof. The additive may be supported to the fiber surface or may be contained in the fiber.

The fibrous sheet constituted of the nonwoven fabric containing the crimped fibers can be suitably produced by a method including a step (web formation step) of forming fibers containing the above-described conjugated fibers (latently crimped fibers) into a web and a step (heating step) of heating the fibrous web and crimping the conjugated fibers.

As a method of forming the fibrous web in the web formation step, it is possible to use a commonly used method such as a direct method including a spunbond method or a melt-blow method, a carding method using melt-blow fibers, staple fibers, or the like, or a dry method such as an air-lay method. Among them, a carding method using melt-blow fibers or staple fibers, particularly, a carding method using staple fibers is commonly used. Examples of the web obtained by using staple fibers include a random web, a semi-random web, a parallel web, and a cross-wrap web.

Prior to the heating step, an entangling step of entangling at least some fibers in the fibrous web may be carried out. A nonwoven fabric in which crimped fibers are suitably entangled can be obtained in the next heating step by carrying out the entangling step. Although the entangling method may be a method of mechanically performing entanglement, preferred is a method of performing entanglement by spraying or injecting (blowing) water. The entanglement of the fibers with water flow is advantageous in increasing the density of the entanglement by crimping in the heating step. Although the water to be sprayed or injected may be blown from one or both sides of the fibrous web, it is preferable to blow water from both sides from the viewpoint of efficiently performing strong entanglement.

A jetting pressure of water in the entangling step is, for example, greater than or equal to 2 MPa, preferably 3 to 12 MPa, more preferably 4 to 10 MPa, so that the fiber entanglement falls within an appropriate range. A temperature of the sprayed or injected water is, for example, 5 to 50° C., and preferably 10 to 40° C.

As a method of spraying or injecting water, preferred is a method of injecting water with use a nozzle or the like having a regular spray area or spray pattern, from the viewpoint of convenience and the like. Specifically, water can be injected onto a fibrous web transferred by a belt conveyor such as an endless conveyor, while the fibrous web is placed on a conveyor belt. The conveyor belt may be water-permeable, and water may pass through the water-permeable conveyor belt from the back side of the fibrous web to be injected onto the fibrous web. In order to suppress scattering of fibers due to water injecting, the fibrous web may be wetted with a small amount of water in advance.

As the nozzle for spraying or injecting water, a plate or die having predetermined orifices successively arranged in a width direction thereof is used, and the plate or die may be disposed to arrange the orifices in the width direction of the fibrous web to be conveyed. The number of orifice lines may be at least one, and a plurality of orifice lines may be arranged in parallel. A plurality of nozzle dies each having one orifice line may be installed in parallel.

Prior to the entangling step, a step (uneven distribution step) of unevenly distributing the fibers in the fibrous web in the plane may be provided. When this step is carried out, a region where fiber density becomes sparse is formed in the fibrous web, and therefore, in the case where the entangling step is water flow entanglement, a water flow can be efficiently injected into the fibrous web, so that moderate entanglement can be easily realized not only on a surface of the fibrous web but also inside thereof.

The uneven distribution step can be performed by spraying or injecting low-pressure water onto the fibrous web. The low-pressure water may be successively sprayed or injected onto the fibrous web, but it is preferable that the low-pressure water is intermittently or periodically sprayed onto the fibrous web. When water is intermittently or periodically sprayed onto the fibrous web, it is possible to periodically and alternately form a plurality of low-density portions and a plurality of high-density portions.

It is desirable that a jetting pressure of water in the uneven distribution step is as low as possible, and the jetting pressure of water is, for example, 0.1 to 1.5 MPa, preferably 0.3 to 1.2 MPa, more preferably 0.6 to 1.0 MPa. A temperature of the sprayed or injected water is, for example, 5 to 50° C., and preferably 10 to 40° C.

As a method of spraying or injecting water intermittently or periodically, there is no particular limitation as long as it is a method capable of periodically and alternately forming a gradient of density on the fibrous web: however, from the viewpoint of convenience and the like, preferred is a method of injecting water through a plate-like object (e.g., porous plate) having a regular spray area or spray pattern formed with a plurality of holes.

In the heating step, the fibrous web is heated with high temperature steam and crimped. In the method of treating the fibrous web with high temperature steam, the fibrous web is exposed to a high temperature or superheated steam (high pressure steam) flow, whereby coil crimps occur in the conjugated fibers (latently crimped fibers). The fibrous web has air permeability. Accordingly, high temperature steam permeates into the fibrous web even in treatment from one direction, substantially uniform crimps are expressed in the thickness direction, and the fibers are uniformly entangled with each other.

The fibrous web shrinks simultaneously with high temperature steam treatment. Accordingly, it is desirable that the fibrous web to be supplied is overfed according to the area shrinkage ratio of an intended nonwoven fabric immediately before the fibrous web is exposed to high temperature steam. A ratio of the overfeeding is 110 to 300%, preferably 120 to 250%, based on the length of the intended nonwoven fabric.

In order to supply the fibrous web with steam, a commonly used steam injecting apparatus may be used. The steam injecting apparatus is preferably an apparatus capable of generally uniformly blowing steam over the whole width of the fibrous web with a desired pressure and amount. The steam injecting apparatus may be provided only on one surface side of the fibrous web, or in order to treat the front and back of the fibrous web with steam at a time, the steam spraying apparatus may be further provided on the other surface side.

Since the high temperature steam injected from the steam injecting apparatus is a gas flow, the high temperature steam enters inside the fibrous web without significantly moving the fibers in the fibrous web, unlike the water flow entanglement treatment and the needle punching treatment. By virtue of the entry action of the steam flow into the fibrous web, the steam flow efficiently covers a surface of each fiber existing in the fibrous web, and enables uniform thermal crimping. Since heat can be satisfactorily conducted inside the fibrous web, as compared with the dry heat treatment, the degree of crimping is almost uniform in the plane direction and the thickness direction.

Similarly to the nozzle for water flow entanglement, as a nozzle for injecting high temperature steam, a plate or die having predetermined orifices successively arranged in a width direction thereof is used, and the plate or die may be disposed to arrange the orifices in the width direction of the fibrous web to be conveyed. The number of orifice lines may be at least one, and a plurality of orifice lines may be arranged in parallel. A plurality of nozzle dies each having one orifice line may be installed in parallel.

A pressure of the high temperature steam to be used can be selected from the range of 0.1 to 2 MPa (for example, 0.2 to 1.5 MPa). If the pressure of the steam is too high, the fibers forming the fibrous web may move more than required to cause disturbance of the texture, or the fibers may be intermingled more than required. When the pressure is too weak, it becomes impossible to give the quantity of heat required for expression of crimps of the fibers to the fibrous web, or the steam cannot penetrate the fibrous web and expression of crimps of the fibers in the thickness direction tends to be nonuniform. Although depending on materials of the fibers and the like, a temperature of the high temperature steam can be selected from the range of 70 to 180° C. (for example, 80 to 150° C.). A treatment speed with high temperature steam can be selected from the range of less than or equal to 200 m/minute (for example, 0.1 to 100 m/minute).

After thus causing expression of crimps of the conjugated fiber in the fibrous web, there may be a case where water remains in the nonwoven fabric, and therefore, a drying step of drying the nonwoven may be provided as necessary. Examples of the drying method may include a method using a drying apparatus such as a cylinder dryer or a tenter; a non-contact method such as far infrared ray irradiation, microwave irradiation, or electron beam irradiation; a method of blowing hot air or passing the nonwoven fabric through hot air, and the like.

Examples of a method for satisfying the above formula [A] in the method of producing a fibrous sheet as described above may include a method of adjusting a content ratio of the conjugated fibers and the non-conjugated fibers; a method of adjusting conditions of the high temperature steam (in particular, temperature and/or pressure) used in the heating step; a method of adjusting the drying temperature in the drying step; and the like.

Third Embodiment (1) Characteristics of Fibrous Sheet

A fibrous sheet according to the present embodiment (hereinafter also simply referred to as the "fibrous sheet") is a fibrous sheet capable of being suitably used not only as a general bandage but also as a medical article such as a compression bandage used for hemostasis, compression therapy, and so on. The fibrous sheet has a rectangular sheet shape having a length direction and a width direction such as a tape shape or a belt shape (long shape).

The fibrous sheet has a bending resistance in the width direction of less than or equal to 300 mN/200 mm, preferably less than or equal to 290 mN/200 mm, more preferably less than or equal to 280 mN/200 mm. When a fibrous sheet having a bending resistance in the width direction of less than or equal to 300 mN/200 mm is, for example, wrapped such that its length direction is the wrapping direction, even in the case where the fibrous sheet is wrapped around a site having surface protrusions and recesses (for example, a portion located at a joint part or the like and protruded by a bone inherent in the joint part or the like) with moderate strength, the fibrous sheet can be wrapped along the shape of the surface protrusions and recesses, and is excellent in concavo-convex fitting property. From the viewpoint of the strength of the fibrous sheet, the bending resistance in the width direction is usually greater than or equal to 30 mN/200 mm and preferably greater than or equal to 50 mN/200 mm.

The phrase "wrapped such that the length direction is the wrapping direction" is a usual mode when a long object such as a bandage is wrapped around an object to be wrapped. The case where the object to be wrapped is a finger is exemplified, a long bandage is wrapped around the finger such that the width direction of the bandage and the length direction of the finger are parallel or approximately parallel to each other.

Conventionally, there has been known a bandage to which stretchability has been imparted in the length direction by various methods: however, as a result of a study made by the present inventors, it has been found that even when the stretchability in the length direction is increased or only the stretchability in the length direction is increased, the concavo-convex fitting property cannot be satisfactorily improved. On the other hand, the present invention is based on the knowledge that attention is paid in the width direction rather than the length direction, and the bending resistance in the width direction unexpectedly becomes an important factor for improving the concavo-convex fitting property.

To reduce the bending resistance in the width direction such that the bending resistance falls within the above range, and meanwhile to make the bending resistance in the length direction larger than the bending resistance in the width direction are effective for achieving a good balance between the concavo-convex fitting property and the strength, consequently the durability of the fibrous sheet. A difference in bending resistance between the length direction and the width direction is, for example, greater than or equal to 10 mN/200 mm, preferably greater than or equal to 30 mN/200 mm, more preferably greater than or equal to 50 mN/200 mm. The fibrous sheet has a bending resistance in the length direction of, for example, 40 to 400 mN/200 mm, preferably 60 to 300 mN/200 mm.

The bending resistance of the fibrous sheet is measured according to the Handle-o-Meter method specified in JIS L 1913. According to the JIS standard, a sample having a width of 200 mm is used.

The fibrous sheet has a compression elastic modulus Pe of preferably less than or equal to 85%, more preferably less than or equal to 80%. When the compression elastic modulus Pe is within this range, it is advantageous for enhancing the concavo-convex fitting property. A lower limit of the compression elastic modulus Pe is not particularly limited, and is, for example, 50%. The compression elastic modulus Pe is calculated in accordance with the "Test methods for nonwovens" specified in JIS L 1913 by the following formula [C]:

$$Pe=\{(T_1'-T)/(T_1-T)\}\times 100 \qquad [C].$$

$T_1$ is the thickness [mm] when an initial load (0.5 kPa) is applied. T is the thickness [mm] when a load of 30 kPa is applied. $T_1'$ is the thickness [mm] when the initial load is restored.

When the fibrous sheet has extensibility, the functionality can be improved when the fibrous sheet is used as, for example, a bandage. By imparting extensibility to the fibrous sheet, the fixing force can be enhanced for example when the fibrous sheet is used for fixing a protective member such as a gauze to an application site. Alternatively, when the fibrous sheet is used for imparting a compression force to an application site by wrapping the fibrous sheet, the compression force can be enhanced. In the case where the fibrous sheet having extensibility is applied to a site to be bent and stretched, such as a joint part, the bending and stretching motion becomes easy. The fibrous sheet having extensibility is further advantageous for improvement of the concavo-convex fitting property.

From the above point of view, the fibrous sheet preferably has extensibility. As described above, in the present specification, "extensible/having extensibility" means that a stress at 50% extension is exhibited in at least one direction (first direction) in the sheet plane. The stress at 50% extension is a stress at extension at the time of extension at 50% elongation (immediately after extension) and is measured by a tensile test in accordance with the "Test methods for nonwovens" specified in JIS L 1913.

From the viewpoint of the concavo-convex fitting property and the easiness of the bending and stretching motion, it is preferable that the fibrous sheet has good extensibility at least in the width direction as the first direction. This width direction may be a direction orthogonal to a flow direction (MD direction) of the fibrous sheet in a production process, that is, a CD direction. A stress at 50% extension in the lateral direction of the fibrous sheet is preferably 0.1 to 20 N/50 mm, more preferably 0.5 to 15 N/50 mm, further preferably 1 to 12 N/50 mm.

On the other hand, it is preferable that the fibrous sheet has good extensibility in the length direction in order to enhance the fixing force and compression force of the fibrous sheet. A stress at 50% extension in the length direction of the fibrous sheet is preferably 0.1 to 50 N/50 mm, more preferably 0.5 to 30 N/50 mm, further preferably 1 to 20 N/50 mm. To increase the stress at 50% extension in the length direction is also advantageous for improvement of the concavo-convex fitting property. The length direction of the fibrous sheet may be a flow direction (MD direction) of the fibrous sheet in a production process. A stress at 50% extension in each direction other than the width direction and the length direction is preferably 0.5 to 60 N/50 mm, more preferably 1 to 45 N/50 mm, further preferably 2 to 40 N/50 mm.

The fibrous sheet preferably exhibits self-adhesiveness. As described above, in the present specification, the "self-adhesiveness" refers to a property allowing fibers on a fibrous sheet surface to engage with each other or come into close contact with each other due to superposition (contact) of the fibers and to be hooked or fixed. The fibrous sheet having self-adhesiveness is advantageous when the fibrous sheet is a bandage or the like. For example, in the case where the fibrous sheet is a bandage, after the bandage is wrapped around an application site, the wrapped fibrous sheets are pressed against each other while being extended by such an operation that an end of the bandage is overlapped on (or torn and then overlapped on) a bandage surface located under the end, so that the fibrous sheets are joined and fixed to each other, thereby expressing self-adhesiveness.

When the fibrous sheet itself has self-adhesiveness, it is unnecessary to form a layer formed of a self-adhesive agent such as an elastomer or a pressure-sensitive adhesive on a surface of the fibrous sheet or to prepare separately a fastener for fixing the tip after wrapping. For example, Japanese Patent Laying-Open No. 2005-095381 (PTD 4) describes that an acrylic polymer (claim 1) or a latex (paragraphs [0004] to [0006]) is caused to adhere as a self-adhesive agent to at least one side of a bandage base material. Formation of a layer formed of an elastomer such as latex on the fibrous sheet surface is effective for enhancing self-adhesiveness.

However, it is preferable that the fibrous sheet according to the present embodiment is constituted only of a nonelastomer material. More specifically, it is preferable that the fibrous sheet is constituted only of fibers. When the layer formed of an elastomer as described above is formed on the fibrous sheet surface or the elastomer is impregnated into a fiber base material, it tends to be relatively difficult to set the bending resistance in the width direction to the above range. The layer formed of an elastomer may induce skin irritation and allergy when wrapped around an application site.

The self-adhesiveness of the fibrous sheet can be evaluated by a curved surface sliding stress. From the viewpoint of the self-adhesiveness, it is preferable that the fibrous sheet has a curved surface sliding stress of, for example, greater than or equal to 3 N/50 mm, preferably greater than or equal to 5 N/50 mm, and the curved surface sliding stress is preferably higher than breaking strength. Since it is relatively easy to unwrap the wrapped fibrous sheet if desired, the curved surface sliding stress is preferably less than or equal to 30 N/50 mm, more preferably less than or equal to 25 N/50 mm. The curved surface sliding stress is measured using a tensile tester in accordance with the method described in Examples section (FIGS. 1 to 3).

The fibrous sheet preferably has a hand cut property. As described above, in the present specification, the "hand cut property" refers to a property enabling breakage (cutting) by hand tension. The hand cut property of the fibrous sheet can be evaluated by breaking strength. From the viewpoint of the hand cut property, the fibrous sheet has a breaking strength in at least one direction in the sheet plane of preferably 5 to 100 N/50 mm, more preferably 8 to 60 N/50 mm, further preferably 10 to 40 N/50 mm. When the breaking strength is within the above range, it is possible to impart a good hand cut property enabling relatively easy breakage (cutting) by hand. If the breaking strength is too large, the hand cut property deteriorates, making it difficult to cut the fibrous sheet with one hand, for example. On the other hand, if the breaking strength is too small, the strength of the fibrous sheet becomes insufficient to cause easy breakage of the fibrous sheet, and durability and handleability are lowered. The breaking strength is measured by a tensile test in accordance with the "Test methods for nonwovens" specified in JIS L 1913.

At least one direction in the sheet plane is a tensile direction when the fibrous sheet is cut by hand, and is preferably the length direction. The length direction may be the MD direction. That is, when the fibrous sheet is used as a bandage, it is usual to break the bandage in the length direction after the bandage is wrapped around an application site while being extended along the length direction thereof, and therefore the direction where the breaking strength is within the above range is preferably the length direction as the tensile direction.

The breaking strength in a direction other than at least one direction in the sheet plane, for example, the width direction or the CD direction is, for example, 0.1 to 300 N/50 mm, preferably 0.5 to 100 N/50 mm, more preferably 1 to 20 N/50 mm.

From the viewpoint of the hand cut property, it is preferable that the fibrous sheet is constituted only of a nonelastomer material. More specifically, it is preferable that the fibrous sheet is constituted only of fibers. If a layer formed of an elastomer, etc. is formed on the fibrous sheet surface, the hand cut property may be lowered.

The fibrous sheet has an elongation at break in at least one direction in the sheet plane of, for example, greater than or equal to 50%, preferably greater than or equal to 60%, more preferably greater than or equal to 80%. When the elongation at break is within the above range, it is advantageous for enhancing the stretchability of the fibrous sheet. The elongation at break in at least one direction in the sheet plane is usually less than or equal to 300% and preferably less than or equal to 250%. The elongation at break is also measured by a tensile test in accordance with the "Test methods for nonwovens" specified in JIS L 1913.

From the viewpoint of the concavo-convex fitting property and the easiness of the bending and stretching motion, at least one direction in the sheet plane is preferably the width direction. From the viewpoint of extensibility in the length direction (for example, from the viewpoint of the fixing force and the compression force described above), at least one direction in the sheet plane is preferably the length direction. The elongation at break in a direction other than at least one direction in the sheet plane is, for example, 10 to 500%/o, preferably 100 to 350%.

The fibrous sheet has a recovery rate after 50% extension in at least one direction in the sheet plane (recovery rate after 50% extension) is preferably greater than or equal to 70% (less than or equal to 100%), more preferably greater than or equal to 80%, further preferably greater than or equal to 90%. When the fibrous sheet having a recovery rate after 50% extension within the range is wrapped around a site having surface protrusions and recesses, such as a joint part, or a site to be bent and stretched, the fibrous sheet is easy to follow the shape of the surface protrusions and recesses of the site and the bending and stretching motion. It is advantageous for improvement of the concavo-convex fitting property and the easiness of the bending and stretching motion, and also advantageous for improvement of the self-adhesiveness due to friction between the overlapped fibrous sheets. If the extension recovery rate is excessively small, the fibrous sheet cannot follow the bending motion of the site, and deformation of the fibrous sheet caused by this motion does not return to its original shape, thus weakening fixation of the wrapped fibrous sheet.

From the viewpoint of the concavo-convex fitting property and the easiness of the bending and stretching motion, at least one direction in the sheet plane is preferably the width direction. From the viewpoint of extensibility in the length direction (for example, from the viewpoint of the fixing force and the compression force described above), at least one direction in the sheet plane is preferably the length direction.

The recovery rate after 50% extension is defined by the following formula:

$$\text{Recovery rate after 50\% extension (\%)} = 100 - X$$

when, in a tensile test in accordance with the "Test methods for nonwovens" specified in JIS L 1913, a residual strain (%) after the test is defined as X when load is removed immediately after the elongation rate reaches 50%.

The recovery rate after 50% extension in a direction other than at least one direction in the sheet plane is, for example, greater than or equal to 70% (less than or equal to 100%), preferably greater than or equal to 80%.

The fibrous sheet has a basis weight of preferably 30 to 300 g/m$^2$, more preferably 50 to 200 g/m$^2$. In order to further improve the concavo-convex fitting property, the basis weight is preferably small, and in this case, the basis weight is preferably less than or equal to 160 g/m$^2$. If the basis weight is excessively small, the strength, consequently the durability of the fibrous sheet is lowered.

The fibrous sheet has a thickness of, for example, 0.2 to 5 mm, preferably 0.3 to 3 mm, more preferably 0.4 to 2 mm. When the basis weight and the thickness are within these ranges, a balance among the concavo-convex fitting property, the ease of bending exhibited when wrapping the fibrous sheet, the extensibility, flexibility, touch feeling and cushioning property of the fibrous sheet is good. A density (bulk density) of the fibrous sheet can be a value corresponding to the above-described basis weight and thickness, and the density (bulk density) is, for example, 0.03 to 0.5 g/cm$^3$, preferably 0.04 to 0.4 g/cm$^3$, more preferably 0.05 to 0.25 g/cm$^3$. From the viewpoint of further improving the concavo-convex fitting property, the density is more preferably less than or equal to 0.2 g/cm$^3$.

The fibrous sheet has an air permeability measured by the Frazier method of preferably greater than or equal to 0.1 cm$^3$/(cm$^2$·second), more preferably 1 to 500 cm$^3$/(cm$^2$·second), further preferably 5 to 300 cm$^3$/(cm$^2$·second), particularly preferably 10 to 200 cm$^3$/(cm$^2$*second). When the air permeability is within this range, the fibrous sheet is more suitably used for the human body, such as a bandage, because the fibrous sheet is good in air permeability and is hardly stuffy.

(2) Structure and Production Method of Fibrous Sheet

The fibrous sheet of the present embodiment is not particularly limited as long as it is constituted of fibers, and the fibrous sheet may be, for example, a woven fabric, a nonwoven fabric, a knit (knitted fabric), or the like. As described above, the fibrous sheet has a rectangular sheet shape having a length direction and a width direction such as a tape shape or a belt shape (long shape). The fibrous sheet may have a single layer structure or a multilayer structure including two or more fibrous layers.

As described above, the fibrous sheet preferably has extensibility. Examples of means for imparting stretchability and extensibility to the fibrous sheet may include 1) a method of subjecting a fibrous sheet substrate such as a woven fabric, a nonwoven fabric, or a knit to gathering; 2) a method of weaving, into a fibrous sheet, yarn formed of a stretchable material such as an elastomer typified by rubber; 3) a method of combining a layer formed of a stretchable material such as an elastomer with a nonstretchable fibrous sheet substrate or impregnating a nonstretchable fibrous sheet substrate with a stretchable material; 4) a method using crimped fibers crimped into a coil shape as at least some fibers constituting a nonwoven fabric; and the like.

Among the above methods, the fibrous sheet according to the present embodiment is preferably obtained by using the method described in 4). Although the gathering described in 1) is effective in that stretchability can be effectively imparted to the fibrous sheet, it is relatively difficult to obtain a fibrous sheet in which the bending resistance in the width direction is within the above range depending on the wavy shape of the gather. According to the methods 2) and 3), while stretchability can be easily imparted to the fibrous sheet, flexibility is lost, and it is relatively difficult to obtain a fibrous sheet in which the bending resistance in the width direction is within the above range.

From the viewpoint of concavo-convex fitting property, ease of bending of a joint part exhibited when the fibrous sheet is wrapped around the joint part, self-adhesiveness, hand cut property, etc., the fibrous sheet is preferably constituted of a nonwoven fabric, namely, the fibrous sheet is preferably a nonwoven fabric sheet.

More preferably, the fibrous sheet is constituted of a nonwoven fabric containing crimped fibers crimped into a coil shape, and still more preferably, the fibrous sheet is constituted of a nonwoven fabric that contains the crimped fibers and that is not subjected to at least one of treatments (desirably all treatments) described in 1) to 3). Particularly preferably, the nonwoven fabric sheet is constituted only of the crimped fibers. Although the fibrous sheet may be constituted of a woven fabric or a knit (knitted fabric), the fineness of yarn (twisted yarn) constituting a woven fabric or a knit (knitted fabric) is relatively large, so that it is relatively difficult to obtain a fibrous sheet having bending resistance in the width direction within the above range. In this regard, when a nonwoven fabric is used, a sheet can be constituted of fibers with smaller fineness, and the concavo-convex fitting property can be further improved.

From the viewpoint of the concavo-convex fitting property, an average fineness of fibers constituting a sheet formed of a nonwoven fabric is preferably less than or equal to 20 dtex, more preferably less than or equal to 15 dtex. The average fineness is preferably greater than or equal to 0.5 dtex, more preferably greater than or equal to 1.0 dtex, from the viewpoint of the strength, consequently the durability of the fibrous sheet.

It is preferable that the fibrous sheet constituted of the nonwoven fabric containing the crimped fibers has a structure in which the respective fibers constituting this nonwoven fabric are not substantially fusion-bonded, but mainly the crimped fibers are entangled with each other at their crimped coil portions and bound or hooked. Further, it is preferable that most (the majority of) crimped fibers (axial direction of crimped fibers) are oriented substantially parallel to a sheet surface. As described above, in the present specification, "oriented substantially parallel to a surface direction" means a state where a portion in which a large number of crimped fibers (axial direction of crimped fibers) are locally oriented along a thickness direction is not repeatedly present, as in for example entanglement by needle punching.

In the fibrous sheet constituted of the nonwoven fabric containing the crimped fibers, the crimped fibers are preferably oriented in a certain direction in the sheet plane (preferably in the length direction), and the adjacent or intersecting crimped fibers are entangled with each other at their crimped coil portions. Even in the thickness direction (or oblique direction) of the fibrous sheet, the crimped fibers are preferably slightly entangled with each other. The entanglement of the crimped fibers can be caused by the process of shrinking a fibrous web as a precursor of the fibrous sheet.

The nonwoven fabric in which crimped fibers (axial direction of crimped fibers) are oriented in a certain direction in the sheet plane and entangled exhibits good stretchability (including extensibility) in this direction. In the case where the certain direction is, for example, the length direction, when a tensile force is applied to the stretchable nonwoven fabric in the length direction, the entangled crimped coil portion tends to extend and return to the original coil shape, so that high stretchability can be exhibited in the length direction. This stretchable nonwoven fabric can exhibit excellent extensibility in a direction (for example, the width direction) orthogonal to the certain direction in the sheet plane. The cushioning property and flexibility in the thickness direction can be expressed by slight entanglement of the crimped fibers in the thickness direction of the nonwoven fabric, whereby the nonwoven fabric can have good touch feeling and texture. The crimped coil portion easily entangles with another crimped coil portion by contact with a certain degree of pressure. The self-adhesiveness can be expressed by the entanglement of the crimped coil portions.

In the fibrous sheet constituted of the nonwoven fabric containing the crimped fibers, when a tensile force is applied to the orientation direction of the crimped fiber (preferably in the length direction), the entangled crimped coil portion extends due to elastic deformation, and when the tensile force is further applied, the fibrous sheet is finally unwrapped, so that the cutting property (hand cut property) is also good.

As described above, the nonwoven fabric capable of constituting the fibrous sheet preferably contains crimped fibers crimped into a coil shape. The crimped fiber is preferably oriented mainly in the surface direction of the nonwoven fabric, and further preferably crimps substantially evenly in the thickness direction. The crimped fiber can be constituted of a conjugated fiber in which a plurality of resins having different thermal shrinkage factors (or thermal expansion coefficients) form a phase structure.

The conjugated fiber constituting the crimped fiber is a fiber (latently crimped fiber) having an asymmetric or layered (so-called bimetal) structure crimped by heating due to a difference in thermal shrinkage factor (or thermal expansion coefficient) of a plurality of resins. The plurality of resins usually have mutually different softening points or melting points. The plurality of resins can be selected from thermoplastic resins such as, for example, polyolefin-based resins (e.g., poly-$C_{2-4}$ olefin-based resins such as low-density, medium-density or high-density polyethylene and polypropylene); acrylic resins (e.g., acrylonitrile-based resins having an acrylonitrile unit, such as acrylonitrile-vinyl chloride copolymers); polyvinyl acetal-based resins (e.g., polyvinyl acetal resins); polyvinyl chloride-based resins (e.g., polyvinyl chloride, vinyl chloride-vinyl acetate copolymers and vinyl chloride-acrylonitrile copolymers); polyvinylidene chloride-based resins (e.g., vinylidene chloride-vinyl chloride copolymers and vinylidene chloride-vinyl acetate copolymers); styrene-based resins (e.g., heat-resistant polystyrene): polyester-based resins (e.g., poly-$C_{2-4}$ alkylene arylate-based resins such as polyethylene terephthalate resins, polytrimethylene terephthalate resins, polybutylene terephthalate resins and polyethylene naphthalate resins); polyamide-based resins (e.g., aliphatic polyamide-based resins such as polyamide 6, polyamide 66, polyamide 11, polyamide 12, polyamide 610 and polyamide 612, semi-aromatic polyamide-based resins, and aromatic polyamide-based resins such as polyphenylene isophthalamide, polyhexamethylene terephthalamide and poly-p-phenylene-terephthalamide); polycarbonate-based resins (e.g., bisphenol A-type polycarbonate); polyparaphenylene benzobisoxazole resins; polyphenylene sulfide resins; polyurethane-based resins; and cellulose-based resins (e.g., cellulose esters). These thermoplastic resins may contain other copolymerizable units.

Among the thermoplastic resins, non thermal adhesive resins under moisture (or heat-resistant hydrophobic resins or nonaqueous resins) having a softening point or melting point greater than or equal to 100° C., such as, for example, polypropylene-based resins, polyester-based resins and polyamide-based resins are preferable because fibers are not melted or softened to be fused even when subjected to a heating treatment with high-temperature steam. Particularly, aromatic polyester-based resins and polyamide-based resins are preferable because they are excellent in balance among heat resistance, fiber formability, and so on. A resin exposed to surfaces of conjugated fibers constituting a nonwoven fabric (latently crimped fiber) is preferably at least a non thermal adhesive resin under moisture so that the conjugated fibers are not fused even when treated with high-temperature steam.

The plurality of resins forming the conjugated fiber may have different thermal shrinkage factors, and may be a combination of resins of the same kind, or a combination of different kinds of resins.

Preferably, the plurality of resins forming the conjugated fiber are a combination of resins of the same kind from the viewpoint of adhesiveness. In the case of the combination of resins of the same kind, usually a combination of a component (A) forming a homopolymer (essential component) and a component (B) forming a modification polymer (copolymer) is used. That is, for example, a copolymerizable monomer for reducing the crystallization degree, the melting point, the softening point, or the like is copolymerized with the homopolymer as an essential component to perform modification, whereby the crystallization degree may be reduced as compared to the homopolymer, or the polymer may be made noncrystalline to reduce the melting point or softening point as compared to the homopolymer. When the crystallization degree, the melting point, or the softening point is changed as described above, this can cause a difference in thermal shrinkage factor. The difference in melting point or softening point is, for example, 5 to 150° C., and preferably 40 to 130° C., more preferably 60 to 120° C. A ratio of the copolymerizable monomer to be used for modification is, for example, 1 to 50 mol %, preferably 2 to 40 mol %, more preferably 3 to 30 mol % (particularly 5 to 20 mol %) based on the whole amount of monomers. While a mass ratio between the component forming a homopolymer and the component forming a modification polymer can be selected according to the structure of fibers, the homopolymer component (A)/the modification polymer component (B) is for example 90/10 to 10/90, and preferably 70/30 to 30/70, more preferably 60/40 to 40/60.

The conjugated fiber is preferably a combination of aromatic polyester-based resins, more preferably a combination of a polyalkylene arylate-based resin (a) and a modified polyalkylene arylate-based resin (b) because latently crimpable conjugated fibers are easily produced. The polyalkylene arylate-based resin (a) can be a homopolymer of an aromatic dicarboxylic acid (e.g., a symmetric aromatic dicarboxylic acid such as terephthalic acid or naphthalene-2,6-dicarboxylic acid) and an alkanediol component (e.g., $C_{2-6}$ alkanediol such as ethylene glycol or butylene glycol). Specifically, a poly-$C_{2-4}$ alkylene terephthalate-based resin such as polyethylene terephthalate (PET) or polybutylene terephthalate (PBT), or the like is used, and usually, PET for use in general PET fibers having an intrinsic viscosity of 0.6 to 0.7 is used.

On the other hand, in the modified polyalkylene arylate-based resin (b), examples of a copolymerization component for reducing the melting point or softening point and the crystallization degree of the polyalkylene arylate-based resin (a) as an essential component include dicarboxylic acid components such as an asymmetric aromatic dicarboxylic acid, an alicyclic dicarboxylic acid and an aliphatic dicarboxylic acid; an alkanediol component having a chain length longer than that of alkanediol of the polyalkylene arylate-based resin (a); and/or an ether bond-containing diol component. The copolymerization components may be used singly, or in combination of two or more kinds thereof. Among these components, as the dicarboxylic acid component, asymmetric aromatic dicarboxylic acids (e.g., isophthalic acid, phthalic acid and 5-sodium sulfoisophthalic acid), aliphatic dicarboxylic acids ($C_{6-12}$ aliphatic dicarboxylic acids such as adipic acid), or the like are generally used. As the diol component, alkanediols (e.g., $C_{3-6}$ alkanediols such as 1,3-propanediol, 1,4-butanediol, 1,6-hexanediol and neopentyl glycol), polyoxyalkylene glycols (e.g., polyoxy-$C_{2-4}$ alkylene glycols such as diethylene glycol, triethylene glycol, polyethylene glycol and polytetramethylene glycol) or the like are generally used. Among them, asymmetric aromatic dicarboxylic acids such as isophthalic acid, and polyoxy-$C_{2-4}$ alkylene glycols such as diethylene glycol are preferable. The modified polyalkylene arylate-based resin (b) may be an elastomer having a $C_{2-4}$ alkylene arylate (e.g., ethylene terephthalate or butylene terephthalate) as a hard segment and a polyoxyalkylene glycol or the like as a soft segment.

In the modified polyalkylene arylate-based resin (b), a ratio of the dicarboxylic acid component (e.g., isophthalic acid) for reducing the melting point or softening point is, for example, 1 to 50 mol %, preferably 5 to 50 mol %, more preferably 15 to 40 mol % based on the whole amount of dicarboxylic acid components constituting the modified polyalkylene arylate-based resin (b). A ratio of the diol component (e.g., diethylene glycol) for reducing the melting point or softening point is, for example, less than or equal to 30 mol %, preferably less than or equal to 10 mol % (e.g., 0.1 to 10 mol %) based on the whole amount of diol components constituting the modified polyalkylene arylate-based resin (b). If the ratio of copolymerization components is too low, sufficient crimps are not expressed, and thus the form stability and stretchability of the nonwoven fabric after expression of crimps are lowered. On the other hand, if the ratio of copolymerizable components is too high, although crimp expressing performance is improved, it is difficult to stably perform spinning.

The modified polyalkylene arylate-based resin (b) may include, as monomer components, polyvalent carboxylic acid components such as trimellitic acid and pyromellitic acid, polyol components such as glycerol, trimethylolpropane, trimethylolethane and pentaerythritol, and so on as necessary.

A transverse cross-sectional shape of the conjugated fiber (cross-sectional shape perpendicular to the longitudinal direction of the fiber) is not limited to a general solid cross-sectional shape such as a circular cross-sectional shape or an irregular cross-sectional shape [flat shape, elliptical shape, polygonal shape, 3 to 14-foliated shape, T-shape, H-shape, V-shape, dog-bone (I-shape) or the like], and it may be a hollow cross-sectional shape or the like. Usually, the transverse cross-sectional shape of the conjugated fiber is a circular cross-sectional shape.

Examples of the transverse cross-sectional structure of the conjugated fiber include phase structures formed of a plurality of resins, such as, for example, structures of core-sheath type, sea-island type, blend type, parallel type (side-by-side type or multilayer lamination type), radial type (radial lamination type), hollow radial type, block type, random composite type and the like. In particular, a structure in which phase parts neighbor each other (so-called bimetal structure), and a structure in which a phase structure is asymmetric, such as, for example, a structure of eccentric core-sheath type or parallel type are preferable because spontaneous crimps are easily expressed by heating.

In the case where the conjugated fiber has a structure of core-sheath type such as a structure of eccentric core-sheath type, the core part may be made from a thermal adhesive resin under moisture (e.g., a vinyl alcohol-based polymer such as an ethylene-vinyl alcohol copolymer or polyvinyl alcohol), or a thermoplastic resin having a low melting point or softening point (e.g., polystyrene or low-density polyethylene) as long as there is a difference in thermal shrinkage with the non thermal adhesive resin under moisture of the sheath part situated at the surface, and thus the fiber can be crimped.

The conjugated fibers have an average fineness of, for example, 0.1 to 20 dtex, preferably 0.5 to 10 dtex, more preferably 1 to 5 dtex. If the fineness is too small, it is difficult to produce fibers themselves, and, in addition, it is difficult to secure fiber strength. Further, it is difficult to express fine coil-shaped crimps in a process of expressing crimps. On the other hand, if the fineness is too large, it becomes difficult to adjust the bending resistance in the width direction to the above range, and in addition, it becomes difficult to express sufficient crimps.

The conjugated fibers have an average fiber length of, for example, 10 to 100 mm, and preferably 20 to 80 mm, more preferably 25 to 75 mm. If the average fiber length is too short, it is difficult to form a fiber web, and, in addition, entanglement of crimped fibers is insufficient when crimps are expressed, so that it may be difficult to secure the strength and stretchability of the nonwoven fabric. If the average fiber length is too long, it is difficult to form a fiber web with a uniform basis weight, and further, a large number of entanglements of fibers are expressed at the time of forming the web, so that fibers may obstruct one another at the time of expressing crimps, resulting in difficulty in expression of stretchability. When the average fiber length is within the above range, some fibers crimped on the nonwoven fabric surface are appropriately exposed on the nonwoven fabric surface, so that the self-adhesiveness of the nonwoven fabric can be improved. The average fiber length within the above range is advantageous for obtaining good hand cut property.

The above-described conjugated fiber is a latently crimped fiber, and when the conjugated fibers are heat-treated, crimps are expressed (or appear), and thus the conjugated fibers are fibers having substantially coil-shaped (helical or spiral spring-shaped) three-dimensional crimps.

The number of crimps (number of mechanical crimps) before heating is, for example, 0 to 30 crimps/25 mm, preferably 1 to 25 crimps/25 mm, more preferably 5 to 20 crimps/25 mm. The number of crimps after heating is, for example, greater than or equal to 30 crimps/25 mm (for example 30 to 200 crimps/25 mm), and preferably 35 to 150 crimps/25 mm.

As described above, the crimped fibers constituting the nonwoven fabric have substantially coil-shaped crimps after expression of crimps. An average curvature radius of circles formed by the coils of the crimped fibers is, for example, 10 to 250 μm, and preferably 20 to 200 μm, more preferably 50 to 160 µm. The average curvature radius is an index expressing an average size of circles formed by the coils of crimped fibers, and in the case where this value is large, the formed coil has a loose shape, i.e., a shape having a small number of crimps. If the number of crimps is small, the number of entanglements of crimped fibers also decreases, and it is difficult to recover the shape against deformation of the coil shape, so that it is disadvantageous for expressing sufficient stretching performance. If the average curvature radius is too small, crimped fibers are not satisfactorily entangled with each other, so that it is difficult to secure web strength. Further, when the coil shape is deformed, stress is too large and breaking strength is excessively increased, so that it is difficult to obtain suitable stretchability.

In the crimped fibers, an average pitch (average crimp pitch) of the coil is, for example, 0.03 to 0.5 mm, preferably 0.03 to 0.3 mm, more preferably 0.05 to 0.2 mm. If the average pitch is excessively large, the number of coil crimps that can be expressed per fiber decreases, so that sufficient stretchability cannot be exhibited. If the average pitch is excessively small, crimped fibers are not satisfactorily entangled with each other, so that it becomes difficult to secure the strength of the nonwoven fabric.

The nonwoven fabric (fibrous web) may contain other fibers (non-conjugated fibers) in addition to the above-described conjugated fibers. Specific examples of the non-conjugated fiber include, in addition to fibers constituted of the above-described non thermal adhesive resin under moisture or thermal adhesive resin under moisture, fibers constituted of cellulose-based fibers [e.g., natural fibers (e.g., cotton, wool, silk, and hemp), semi-synthetic fibers (e.g., acetate fibers such as triacetate fibers), and regenerated fibers (e.g., rayon, polynosic, cupra, and lyocell (e.g., registered trademark "Tencel"))] and the like. An average fineness and average fiber length of the non-conjugated fibers can be the same as those of the conjugated fibers. The non-conjugated fibers may be used singly, or in combination of two or more kinds thereof.

A ratio (mass ratio) of the conjugated fiber and the non-conjugated fiber is preferably adjusted appropriately so that the bending resistance in the width direction falls within the above-described range. As the ratio, the conjugated fiber/the non-conjugated fiber is, for example, 50/50 to 100/0, and preferably 60/40 to 100/0, more preferably 70/30 to 100/0, still more preferably 80/20 to 100/0, particularly preferably 90/10 to 100/0. A balance between the strength and stretchability or flexibility of the nonwoven fabric can be adjusted by blending the non-conjugated fibers.

The nonwoven fabric (fibrous web) may contain commonly used additives, such as stabilizers (e.g., thermal stabilizers, ultraviolet absorbers, light stabilizers, and antioxidants), antibacterial agents, deodorants, fragrances, colorants (dyes and pigments), fillers, antistatic agents, flame retardants, plasticizers, lubricants, and crystallization speed retardants. The additives may be used singly, or in combination of two or more kinds thereof. The additive may be supported to the fiber surface or may be contained in the fiber.

The fibrous sheet constituted of the nonwoven fabric containing the crimped fibers can be suitably produced by a method including a step (web formation step) of forming fibers containing the above-described conjugated fibers (latently crimped fibers) into a web and a step (heating step) of heating the fibrous web and crimping the conjugated fibers.

As a method of forming the fibrous web in the web formation step, it is possible to use a commonly used method such as a direct method including a spunbond method or a melt-blow method, a carding method using melt-blow fibers, staple fibers, or the like, or a dry method such as an air-lay method. Among them, a carding method using melt-blow fibers or staple fibers, particularly, a carding method using staple fibers is commonly used. Examples of the web obtained by using staple fibers include a random web, a semi-random web, a parallel web, and a cross-wrap web.

Prior to the heating step, an entangling step of entangling at least some fibers in the fibrous web may be carried out. A nonwoven fabric in which crimped fibers are suitably entangled can be obtained in the next heating step by carrying out the entangling step. Although the entangling method may be a method of mechanically performing entanglement, preferred is a method of performing entanglement by spraying or injecting (blowing) water. The entanglement of the fibers with water flow is advantageous in increasing the density of the entanglement by crimping in the heating step. Although the water to be sprayed or injected may be blown from one or both sides of the fibrous web, it is preferable to blow water from both sides from the viewpoint of efficiently performing strong entanglement.

A jetting pressure of water in the entangling step is, for example, greater than or equal to 2 MPa, preferably 3 to 12 MPa, more preferably 4 to 10 MPa, so that the fiber entanglement falls within an appropriate range. A temperature of the sprayed or injected water is, for example, 5 to 50° C., and preferably 10 to 40° C.

As a method of spraying or injecting water, preferred is a method of injecting water with use a nozzle or the like having a regular spray area or spray pattern, from the viewpoint of convenience and the like. Specifically, water can be injected onto a fibrous web transferred by a belt conveyor such as an endless conveyor, while the fibrous web is placed on a conveyor belt. The conveyor belt may be water-permeable, and water may pass through the water-permeable conveyor belt from the back side of the fibrous web to be injected onto the fibrous web. In order to suppress scattering of fibers due to water injecting, the fibrous web may be wetted with a small amount of water in advance.

As the nozzle for spraying or injecting water, a plate or die having predetermined orifices successively arranged in a width direction thereof is used, and the plate or die may be disposed to arrange the orifices in the width direction of the fibrous web to be conveyed. The number of orifice lines may be at least one, and a plurality of orifice lines may be arranged in parallel. A plurality of nozzle dies each having one orifice line may be installed in parallel.

Prior to the entangling step, a step (uneven distribution step) of unevenly distributing the fibers in the fibrous web in the plane may be provided. When this step is carried out, a region where fiber density becomes sparse is formed in the fibrous web, and therefore, in the case where the entangling step is water flow entanglement, a water flow can be efficiently injected into the fibrous web, so that moderate entanglement can be easily realized not only on a surface of the fibrous web but also inside thereof.

The uneven distribution step can be performed by spraying or injecting low-pressure water onto the fibrous web. The low-pressure water may be successively sprayed or injected onto the fibrous web, but it is preferable that the low-pressure water is intermittently or periodically sprayed onto the fibrous web. When water is intermittently or periodically sprayed onto the fibrous web, it is possible to periodically and alternately form a plurality of low-density portions and a plurality of high-density portions.

It is desirable that a jetting pressure of water in the uneven distribution step is as low as possible, and the jetting pressure of water is, for example, 0.1 to 1.5 MPa, preferably 0.3 to 1.2 MPa, more preferably 0.6 to 1.0 MPa. A temperature of the sprayed or injected water is, for example, 5 to 50° C., and preferably 10 to 40° C.

As a method of spraying or injecting water intermittently or periodically, there is no particular limitation as long as it is a method capable of periodically and alternately forming a gradient of density on the fibrous web; however, from the viewpoint of convenience and the like, preferred is a method of injecting water through a plate-like object (e.g., porous plate) having a regular spray area or spray pattern formed with a plurality of holes.

In the heating step, the fibrous web is heated with high temperature steam and crimped. In the method of treating the fibrous web with high temperature steam, the fibrous web is exposed to a high temperature or superheated steam (high pressure steam) flow, whereby coil crimps occur in the conjugated fibers (latently crimped fibers). The fibrous web has air permeability. Accordingly, high temperature steam permeates into the fibrous web even in treatment from one direction, substantially uniform crimps are expressed in the thickness direction, and the fibers are uniformly entangled with each other.

The fibrous web shrinks simultaneously with high temperature steam treatment. Accordingly, it is desirable that the fibrous web to be supplied is overfed according to the area shrinkage ratio of an intended nonwoven fabric immediately before the fibrous web is exposed to high temperature steam. A ratio of the overfeeding is 110 to 300%, preferably 120 to 250%, based on the length of the intended nonwoven fabric.

In order to supply the fibrous web with steam, a commonly used steam injecting apparatus may be used. The steam injecting apparatus is preferably an apparatus capable of generally uniformly blowing steam over the whole width of the fibrous web with a desired pressure and amount. The steam injecting apparatus may be provided only on one surface side of the fibrous web, or in order to treat the front and back of the fibrous web with steam at a time, the steam spraying apparatus may be further provided on the other surface side.

Since the high temperature steam injected from the steam injecting apparatus is a gas flow, the high temperature steam enters inside the fibrous web without significantly moving the fibers in the fibrous web, unlike the water flow entanglement treatment and the needle punching treatment. By virtue of the entry action of the steam flow into the fibrous web, the steam flow efficiently covers a surface of each fiber existing in the fibrous web, and enables uniform thermal crimping. Since heat can be satisfactorily conducted inside the fibrous web, as compared with the dry heat treatment, the degree of crimping is almost uniform in the plane direction and the thickness direction.

Similarly to the nozzle for water flow entanglement, as a nozzle for injecting high temperature steam, a plate or die having predetermined orifices successively arranged in a width direction thereof is used, and the plate or die may be disposed to arrange the orifices in the width direction of the fibrous web to be conveyed. The number of orifice lines may be at least one, and a plurality of orifice lines may be arranged in parallel. A plurality of nozzle dies each having one orifice line may be installed in parallel.

A pressure of the high temperature steam to be used can be selected from the range of 0.1 to 2 MPa (for example, 0.2 to 1.5 MPa). If the pressure of the steam is too high, the fibers forming the fibrous web may move more than required to cause disturbance of the texture, or the fibers may be intermingled more than required. When the pressure is too weak, it becomes impossible to give the quantity of heat required for expression of crimps of the fibers to the fibrous web, or the steam cannot penetrate the fibrous web and expression of crimps of the fibers in the thickness direction tends to be nonuniform. Although depending on materials of the fibers and the like, a temperature of the high temperature steam can be selected from the range of 70 to 180° C. (for example, 80 to 150° C.). A treatment speed with high temperature steam can be selected from the range of less than or equal to 200 m/minute (for example, 0.1 to 100 m/minute).

After thus causing expression of crimps of the conjugated fiber in the fibrous web, there may be a case where water remains in the nonwoven fabric, and therefore, a drying step of drying the nonwoven may be provided as necessary. Examples of the drying method may include a method using a drying apparatus such as a cylinder dryer or a tenter; a non-contact method such as far infrared ray irradiation, microwave irradiation, or electron beam irradiation; a method of blowing hot air or passing the nonwoven fabric through hot air, and the like.

Examples of a method for adjusting the bending resistance in the width direction to the above-described range in the method of producing a fibrous sheet may include a method of adjusting a content ratio of the conjugated fibers and the non-conjugated fibers; a method of adjusting conditions of the high temperature steam (in particular, temperature and/or pressure) used in the heating step; a method of adjusting the drying temperature in the drying step; and the like.

EXAMPLES

Hereinafter, the present invention will be described more specifically with reference to examples, but the present invention is not limited by these examples. Physical property values in fibrous sheets (bandages) obtained in Examples and Comparative Examples below were measured by the following methods.

[1] Number of Mechanical Crimps (Crimps/25 mm)

The number of machine crimps was measured in accordance with JIS L 1015 "Chemical fiber staple test method" (8.12.1).

[2] Number of Average Coil Crimps (Coil Crimps/Mm)

A crimped fiber (conjugated fiber) was removed with care from a fibrous sheet so as not to stretch coil crimps, and in the same manner as measurement of the number of machine crimps, the number of average coil crimps was measured in accordance with JIS L 1015 "Chemical fiber staple test method" (8.12.1).

[3] Average Crimp Pitch (μm)

At the time of measuring the number of average coil crimps, a distance between successive adjacent coils was measured, and an average crimp pitch was measured as an average value of n=100.

[4] Average Curvature Radius (μm)

A photograph of an arbitrary cross section of a fibrous sheet enlarged 100 times was taken using a scanning electron microscope (SEM). For a fiber forming a spiral (coil) of one or more rounds, among fibers in the photograph of the cross section thus taken, the radius of a circle when the circle was described along the spiral (the radius of a circle when a crimped fiber was observed in a coil axial direction) was determined as a curvature radius (μm). When a fiber drew a spiral ovally, ½ of the sum of the major axis and the minor axis of the oval was determined as the curvature radius. However, for excluding the case where sufficient coiled crimps were not expressed in the crimped fiber, or the case where the spiral form of the fiber was seen as an oval because it was observed diagonally, only ovals having a ratio between the major axis and the minor axis falling within the range of 0.8 to 1.2 were selected as objects to be measured. An average curvature radius (μm) was determined as an average value of n=100.

[5] Basis Weight (g/m$^2$)

A basis weight was measured in accordance with the "Test methods for nonwovens" specified in JIS L 1913.

[6] Thickness (Mm) and Density (g/Cm$^3$)

In Examples and Comparative Examples (Examples 1 to 4, Comparative Example 1) according to the first embodiment and Examples and Comparative Examples (Examples 7 and 8, Comparative Examples 5 and 6) according to the third embodiment, a thickness of a fibrous sheet was measured in accordance with the "Test methods for nonwovens" specified in JIS L 1913, and a density was calculated from this value and the basis weight measured by the method of [5].

In Examples and Comparative Examples (Examples 5 and 6, Comparative Examples 2 to 4) according to the second embodiment, a thickness $T_1$ of a single fibrous sheet was measured in accordance with the A method specified in JIS L 1913 (load: 0.5 kPa). A thickness $T_3$ of three superimposed fibrous sheets was measured under the same conditions. From these measured values, $\{T_3/(3 \times T_1)\} \times 100$ as the left side of the above formula [A] was calculated. A density (g/cm$^3$) was calculated from the basis weight measured by the method of [5] and the thickness $T_1$ measured by the above method.

[7] Bending Resistance (mN/200 mm) in Examples and Comparative Examples (Examples 7 and 8, Comparative Examples 5 and 6) According to Third Embodiment A bending resistance was measured in accordance with the Handle-o-Meter method in the "Test methods for nonwovens" specified in JIS L 1913. The width of a measurement sample was set to 200 mm. The bending resistance was measured for each of the length direction (MD direction) and the width direction (CD direction) of a fibrous sheet.

[8] Breaking Strength (N/50 mm) and Elongation at Break (%)

A basis weight was measured in accordance with the "Test methods for nonwovens" specified in JIS L 1913. The bending resistance was measured for each of the length direction (MD direction) and the width direction (CD direction) of a fibrous sheet.

[9] Stress $S_0$(N/50 mm) at Initial Extension, Stress $S_5$(N/50 mm) at Extension after Five Minutes, and Stress Relaxation Rate (%) in Examples and Comparative Examples (Examples 1 to 4, Comparative Example 1) According to First Embodiment A stress $S_0$ at initial extension as the stress at extension immediately after extension in the length direction (MD direction) at 50% elongation and a stress $S_5$ at extension after five minutes as the stress at extension generated when the sheet was extended in the length direction (MD direction) at 50% elongation and held in this state for five minutes were measured in accordance with the "Test methods for nonwovens" specified in JIS L 1913, and a stress relaxation rate was calculated in accordance with the formula defined above.

[10] Stress at 50% Extension (N/50 mm) in Examples and Comparative Examples (Examples 5 and 6, Comparative Examples 2 to 4) According to Second Embodiment and Examples and Comparative Examples (Examples 7 and 8, Comparative Examples 5 and 6) According to Third Embodiment A basis weight was measured in accordance with the "Test methods for nonwovens" specified in JIS L 1913. The bending resistance was measured for each of the length direction (MD direction) and the width direction (CD direction) of a fibrous sheet. In Examples and Comparative Examples (Examples 5 and 6, Comparative Examples 2 to 4) according to the second embodiment, a stress at 50% extension in the width direction (first direction, CD direction) of a fibrous sheet is represented by $S_1$, and a stress at 50% extension in the length direction (second direction, MD direction) is represented by $S_2$.

[11] Recovery Rate after 50% Extension

A tensile test in accordance with the "Test methods for nonwovens" specified in JIS L 1913 was carried out, and
  a recovery rate after 50% extension was obtained based on the following formula:

Recovery rate (%) after 50% extension=100–X.

In the formula, X represents a residual strain (%) after the tensile test when load is removed immediately after the elongation rate has reached 50% in the test. The recovery rates after 50% extension was measured for each of the length direction (MD direction) and the width direction (CD direction) of a fibrous sheet.

[12] Compression Elastic Modulus Pe (%) in Examples and Comparative Examples (Examples 5 and 6, Comparative Examples 2 to 4) According to Second Embodiment and Examples and Comparative Examples (Examples 7 and 8, Comparative Examples 5 and 6) According to Third Embodiment A compression elastic modulus Pe was calculated based on the above formula [C] in accordance with the "Test methods for nonwovens" specified in JIS L 1913.

[13] Thickness Difference ΔT (Mm) in Examples and Comparative Examples (Examples 5 and 6, Comparative Examples 2 to 4) According to Second Embodiment A thickness difference ΔT was obtained as ($T_1$-T) in the above formula [C].

[14] Curved Surface Sliding Stress (N/50 mm)

First, a fibrous sheet was cut into a size of 50 mm in width and 600 mm in length so that the MD direction was the length direction, to obtain a sample 1. Then, as shown in FIG. 1(a), one end of the sample 1 was fixed to a winding core 3 (a pipe roll formed of a polypropylene resin and having an outer diameter of 30 mm and a length of 150 mm) with a single-sided adhesive tape 2. Then, with use of an alligator clip 4 (the gripping width was 50 mm, and a rubber sheet having a thickness of 0.5 mm had been fixed on the inside of the clip with a double-sided adhesive tape before use), a weight 5 with 150 g was attached to the other end of the sample 1 to apply load to the whole width of the sample 1 evenly.

Then, while the winding core 3 to which the sample 1 was fixed was lifted up such that the sample 1 and the weight 5 were suspended, the winding core 3 was rotated for five rounds so that the weight 5 did not significantly swing, to wind up the sample 1 and thus to lift up the weight 5 (see FIG. 1(b)). In this state, a contact between a cylindrical portion at an outermost peripheral portion of the sample 1 wrapped around the winding core 3 and a planar portion of the sample 1 unwrapped around the winding core 3 was defined as a base point 6 (the contact was a border line between an area of the sample 1 wrapped around the winding core 3 and an area of the sample 1 rendered vertical by the gravity of the weight 5), and the alligator clip 4 and the weight 5 were quietly removed so as not to move and shift the base point 6. Then, the outermost peripheral portion of the sample 1 wound around the winding core 3 was cut with a razor at a point 7 that was located a half-circle away (180°) from the base point 6 along the sample 1, paying attention to avoid cutting underlying the sample 1, to provide a cut 8 (see FIG. 2).

A curved surface sliding stress between an outermost layer portion in the sample 1 and an inner layer portion placed under the outermost layer portion (inner layer) and wrapped around the winding core 3 was measured. For this measurement, a tensile tester ("Autograph" manufactured by Shimadzu Corporation) was used. The winding core 3 was fixed on a jig 9 installed on a chuck base on a fixed side of the tensile tester (see FIG. 3), and the end of the sample 1 (the end to which the alligator clip 4 had been attached) was gripped by a chuck 10 on a load cell side to stretch the sample 1 at a tensile speed of 200 mm/minute. When the sample 1 was removed (separated) at the cut 8, the measured value (tensile strength) was regarded as the curved surface sliding stress.

1. Production of Fibrous Sheet (First Embodiment)

Example 1

As a latently crimpable fiber, a side-by-side type composite staple fiber ["Sofit PN780" manufactured by Kuraray Co., Ltd., 1.7 dtex×51 mm long, number of machine crimps: 12 crimps/25 mm, number of crimps after heat treatment at 130° C. for 1 minute: 62 crimps/25 mm] was prepared that was constituted of a polyethylene terephthalate resin having an intrinsic viscosity of 0.65 [component (A)] and a modified polyethylene terephthalate resin [component (B)] in which 20 mol % of isophthalic acid is copolymerized with 5 mol % of diethylene glycol. Using 100% by mass of this side-by-side type composite staple fiber, a carded web having a basis weight of 30 g/m$^2$ was provided by a carding method.

This carded web was moved on a conveyer net, and allowed to pass between the conveyer net and a porous plate drum with pores (circular form) having a diameter of 2 mmφ and a pitch of 2 mm and being arranged in a hound's-tooth check pattern. From the inside of the porous plate drum, a water flow was injected in a spray form at 0.8 MPa toward the web and the conveyer net, and thus an uneven distribution step for periodically forming a low-density region and a high-density region of fibers was conducted.

Then, the carded web was transferred to a heating step while the web was overfed at about 200% without prevention of contraction in the heating step due to steam.

Then, the carded web was introduced to a steam injecting apparatus provided in a belt conveyer, and steam at 0.5 MPa and a temperature of about 160° C. was ejected to the carded web perpendicularly from the steam injecting apparatus to treat the web with steam, so that coil-shaped crimps of the latently crimped fibers were expressed, and at the same time, the fibers were entangled. In this steam injecting apparatus, nozzles were installed in one of the conveyers so as to blow steam toward the carded web through the conveyer belt. Each of the steam injecting nozzles had a pore diameter of 0.3 mm, and an apparatus in which the nozzles were arranged in a line at a pitch of 2 mm in the width direction of the conveyer was used. The processing speed was 8.5 m/min, and the distance between each nozzle and the conveyor belt on a suction side was 7.5 mm. Finally, the web was dried with hot air at 120° C. for 1 minute to obtain a stretchable fibrous sheet.

Observation of a surface and cross section in the thickness direction of the obtained fibrous sheet under an electron microscope (100 magnifications) revealed that fibers were oriented substantially parallel with the plane direction of the fibrous sheet, and crimped substantially uniformly in the thickness direction.

Example 2

A stretchable fibrous sheet was produced in the same manner as in Example 1 except that the hot air drying temperature was set to 140° C. Observation of a surface and cross section in the thickness direction of the obtained fibrous sheet under an electron microscope (100 magnifications) revealed that fibers were oriented substantially parallel with the plane direction of the fibrous sheet, and crimped substantially uniformly in the thickness direction. In Examples 1 and 2 and Comparative Example 1 to be described later, carded webs used had the same basis weight (30 g/m$^2$).

Example 3

A commercially available polyurethane meltblown nonwoven fabric ("Meltblown UC0060" manufactured by Kuraray Kuraflex Co., Ltd.) was thermally embossed and bonded at a treatment temperature of 130° C., while being extended 1.5 times, onto one side of a commercially available polyester spunbond nonwoven fabric ("ecule 3201A" manufactured by Toyobo Co., Ltd.) having a three-layer structure of spunbond nonwoven fiber layer/meltblown nonwoven fiber layer/spunbond nonwoven fiber layer, and the resultant was subjected to gathering by relaxing the extension, so that a stretchable fibrous sheet was produced.

Example 4

A carded web having a basis weight of 30 g/m$^2$ was produced in the same manner as in Example 1 except that 80% by mass of the latently crimpable fibers used in Example 1 and 20% by mass of heat-fusible fibers ("Sofista S220" manufactured by Kuraray Co., Ltd., 3.3 dtex×51 mm long) were used as fibers constituting a carded web, and a stretchable fibrous sheet was produced in the same manner as in Example 1 except that this carded web was used.

Comparative Example 1

A stretchable fibrous sheet was produced in the same manner as in Example 1 except that the hot air drying temperature was set to 160° C. Observation of a surface and cross section in the thickness direction of the obtained fibrous sheet under an electron microscope (100 magnifications) revealed that fibers were oriented substantially parallel with the plane direction of the fibrous sheet, and crimped substantially uniformly in the thickness direction.

2. Evaluation of Fibrous Sheet (First Embodiment)

Each of the obtained fibrous sheets was subjected to the following evaluation test.

(1) Seaming Feeling Evaluation Test

A fibrous sheet having a width of 2.5 cm was wrapped three times around the second joint part of a forefinger while being stretched by 30%, and after 5 minutes, the presence or absence of a color change of the fingertip was visually observed, and the presence or absence of pain at the fingertip was confirmed.

(2) Wrapping Stability Evaluation Test

A fibrous sheet having a width of 2.5 cm was wrapped three times around the second joint part of a forefinger while being stretched by 30%, and after 5 minutes, the wearer bent and stretched the forefinger ten times to check whether or not the fibrous sheet was loosened (shifted or peeled).

of the latently crimped fibers were expressed, and at the same time, the fibers were entangled. In this steam injecting apparatus, nozzles were installed in one of the conveyers so as to blow steam toward the carded web through the conveyer belt. Each of the steam injecting nozzles had a pore diameter of 0.3 mm, and an apparatus in which the nozzles were arranged in a line at a pitch of 2 mm in the width direction of the conveyer was used. The processing speed was 8.5 m/min, and the distance between each nozzle and

TABLE 1

| | | Example 1 | Example 2 | Example 3 | Example 4 | Comparative Example 1 |
|---|---|---|---|---|---|---|
| Number of average coil crimps | (crimps/mm) | 8.3 | 26.3 | — | 5.5 | 38.5 |
| Average crimp pitch | (μm) | 120 | 38 | — | 181 | 26 |
| Average curvature radius | (μm) | 62.8 | 52.5 | — | 65.6 | 27.6 |
| Basis weight | (g/m$^2$) | 86.0 | 148.7 | 145.9 | 71.7 | 173.0 |
| Thickness | (mm) | 1.13 | 1.35 | 1.70 | 0.95 | 1.39 |
| Density | (g/cm$^3$) | 0.08 | 0.11 | 0.09 | 0.08 | 0.12 |
| Breaking strength | MD (N/50 mm) | 13.5 | 22.8 | 59.7 | 34.5 | 30.5 |
| | CD (N/50 mm) | 3.9 | 7.1 | 247.9 | 8.8 | 8.7 |
| Elongation at break | MD (%) | 102 | 173 | 245 | 169 | 189 |
| | CD (%) | 108 | 150 | 14 | 101 | 181 |
| Stress $S_0$ at initial extension | MD (N/50 mm) | 5.2 | 5.4 | 4.8 | 4.9 | 5.8 |
| Stress $S_5$ at extension after five minutes | MD (N/50 mm) | 4.1 | 4.4 | 4.0 | 2.7 | 5.3 |
| Stress relaxation rate | (%) | 78.8 | 81.5 | 83.3 | 55.1 | 91.4 |
| Recovery rate after 50% extension | MD (%) | 94.5 | 93.2 | 96.2 | 89.6 | 91.1 |
| | CD (%) | 91.8 | 91.5 | — | 83.5 | 82.6 |
| Curved surface sliding stress | (N/50 mm) | 12.6 | 16.5 | 5.6 | 9.4 | 9.8 |
| Evaluation Feeling of seaming | Presence or absence of color change | Absence | Absence | Absence | Absence | Presence |
| | Presence or absence of pain | Absence | Absence | Absence | Absence | Presence |
| Wrapping stability | Presence or absence of loosening | Absence | Absence | Absence | Presence | Absence |

3. Production of fibrous sheet (Second Embodiment)

Example 5

As a latently crimpable fiber, a side-by-side type composite staple fiber ["Sofit PN780" manufactured by Kuraray Co., Ltd., 1.7 dtex×51 mm long, number of machine crimps: 12 crimps/25 mm, number of crimps after heat treatment at 130° C. for 1 minute: 62 crimps/25 mm] was prepared that was constituted of a polyethylene terephthalate resin having an intrinsic viscosity of 0.65 [component (A)] and a modified polyethylene terephthalate resin [component (B)] in which 20 mol % of isophthalic acid is copolymerized with 5 mol % of diethylene glycol. Using 100% by mass of this side-by-side type composite staple fiber, a carded web having a basis weight of 30 g/m$^2$ was provided by a carding method.

This carded web was moved on a conveyer net, and allowed to pass between the conveyer net and a porous plate drum with pores (circular form) having a diameter of 2 mmφ and a pitch of 2 mm and being arranged in a hound's-tooth check pattern. From the inside of the porous plate drum, a water flow was injected in a spray form at 0.8 MPa toward the web and the conveyer net, and thus an uneven distribution step for periodically forming a low-density region and a high-density region of fibers was conducted.

Then, the carded web was transferred to a heating step while the web was overfed at about 200% without prevention of contraction in the heating step due to steam.

Then, the carded web was introduced to a steam injecting apparatus provided in 15s a belt conveyer, and steam at 0.5 MPa and a temperature of about 160° C. was ejected to the carded web perpendicularly from the steam injecting apparatus to treat the web with steam, so that coil-shaped crimps the conveyor belt on a suction side was 7.5 mm. Finally, the web was dried with hot air at 120° C. for 1 minute to obtain a stretchable fibrous sheet.

Observation of a surface and cross section in the thickness direction of the obtained fibrous sheet under an electron microscope (100 magnifications) revealed that fibers were oriented substantially parallel with the plane direction of the fibrous sheet, and crimped substantially uniformly in the thickness direction.

Example 6

A stretchable fibrous sheet was produced in the same manner as in Example 5 except that the hot air drying temperature was set to 140° C. Observation of a surface and cross section in the thickness direction of the obtained fibrous sheet under an electron microscope (100 magnifications) revealed that fibers were oriented substantially parallel with the plane direction of the fibrous sheet, and crimped substantially uniformly in the thickness direction. In Examples 5 and 6 and Comparative Example 2 to be described later, carded webs used had the same basis weight (30 g/m$^2$).

Comparative Example 2

A stretchable fibrous sheet was produced in the same manner as in Example 5 except that the hot air drying temperature was set to 160° C. Observation of a surface and cross section in the thickness direction of the obtained fibrous sheet under an electron microscope (100 magnifications) revealed that fibers were oriented substantially parallel with the plane direction of the fibrous sheet, and crimped substantially uniformly in the thickness direction.

Comparative Example 3

A carded web having a basis weight of 30 g/m² was produced in the same manner as in Example 5 except that 80% by mass of the latently crimpable fibers used in Example 5 and 20% by mass of heat-fusible fibers ("Sofista S220" manufactured by Kuraray Co., Ltd., 3.3 dtex×51 mm long) were used as fibers constituting a carded web, and a stretchable fibrous sheet was produced in the same manner as in Example 5 except that this carded web was used.

Comparative Example 4

A commercially available polyurethane meltblown nonwoven fabric ("Meltblown UC0060" manufactured by Kuraray Kuraflex Co., Ltd.) was thermally embossed and bonded at a treatment temperature of 130° C., while being extended 1.5 times, onto one side of a commercially available polyester spunbond nonwoven fabric ("ecule 3201A" manufactured by Toyobo Co., Ltd.) having a three-layer structure of spunbond nonwoven fiber layer/meltblown nonwoven fiber layer/spunbond nonwoven fiber layer, and the resultant was subjected to gathering by relaxing the extension, so that a stretchable fibrous sheet was produced.

4. Evaluation of Fibrous Sheet (Second Embodiment)

Each of the obtained fibrous sheets was subjected to the following evaluation test.

(Ease of Bending of Joint Part after Wrapping Fibrous Sheet)

A fibrous sheet having a width of 5 cm was wrapped three times around the second joint part of a forefinger while being stretched by 30%, and when the second joint part was bent, tightness applied to the finger and hardness were evaluated with the following five scores, and an average score of five subjects was obtained. In Comparative Examples 2 to 4, especially Comparative Example 4, when the wearer bent the second joint part, the fibrous sheet was folded into a wrinkle shape (wavy shape) on the inside of the joint part, and it seemed that the joint part was difficult to be bent in appearance.

Score 5: No tightness or hardness was sensed.
Score 4: Little tightness or hardness was sensed.
Score 3: Slight tightness or hardness was sensed.
Score 2: Strong tightness or hardness was sensed.
Score 1: Extremely strong tightness or hardness was sensed.

TABLE 2

|  |  |  | Example 5 | Example 6 | Comparative Example 2 | Comparative Example 3 | Comparative Example 4 |
|---|---|---|---|---|---|---|---|
| Number of average coil crimps |  | (crimps/mm) | 8.1 | 27.9 | 7.1 | 36.6 | — |
| Average crimp pitch |  | (μm) | 123 | 36 | 141 | 27 | — |
| Average curvature radius |  | (μm) | 62.7 | 53.3 | 61.3 | 28.1 | — |
| Basis weight |  | (g/m²) | 91.4 | 150.3 | 71.7 | 172.1 | 165.8 |
| Thickness | $T_1$ | (mm) | 1.15 | 1.32 | 0.95 | 1.33 | 1.56 |
|  | $T_3$ | (mm) | 2.76 | 3.23 | 2.53 | 3.51 | 4.36 |
|  | $\{T_3/(3 \times T_1)\} \times 100$ | (%) | 80.0 | 81.6 | 88.8 | 88.0 | 93.2 |
| Density |  | (g/cm³) | 0.08 | 0.11 | 0.08 | 0.13 | 0.11 |
| Breaking strength |  | MD (N/50 mm) | 14.7 | 23.7 | 34.5 | 30.3 | 74.2 |
|  |  | CD (N/50 mm) | 4.2 | 6.7 | 8.8 | 8.9 | 301.8 |
| Elongation at break |  | MD (%) | 105 | 165 | 169 | 177 | 362 |
|  |  | CD (%) | 103 | 155 | 101 | 165 | 15 |
| Stress at 50% extension | $S_1$ | (N/50 mm) | 1.19 | 1.38 | 5.9 | 4.13 | — |
|  | $S_2$ | (N/50 mm) | 5.21 | 5.39 | 4.7 | 8.51 | 4.79 |
|  | $S_2/S_1$ | — | 4.4 | 3.9 | 0.8 | 2.1 | — |
| Recovery rate after 50% extension |  | MD (%) | 95.4 | 94.2 | 90.5 | 88.9 | 96.8 |
|  |  | CD (%) | 94.6 | 92.1 | 81.6 | 84.2 | — |
| Compression elastic modulus Pe |  | (%) | 76.2 | 81.1 | 89.5 | 87.9 | 86.5 |
| Thickness difference ΔT |  | (mm) | 0.4 | 0.4 | 0.3 | 0.3 | 0.5 |
| Curved surface sliding stress |  | (N/50 mm) | 12.3 | 17.4 | 9.3 | 19.8 | 0.5 |
| Evaluation | Ease of bending | Average score | 4.2 | 4.0 | 2.4 | 2.0 | 1.6 |

5. Production of Fibrous Sheet (Third Embodiment)

Example 7

As a latently crimpable fiber, a side-by-side type composite staple fiber ["Sofit PN780" manufactured by Kuraray Co., Ltd., 1.7 dtex×51 mm long, number of machine crimps: 12 crimps/25 mm, number of crimps after heat treatment at 130° C. for 1 minute: 62 crimps/25 mm] was prepared that was constituted of a polyethylene terephthalate resin having an intrinsic viscosity of 0.65 [component (A)] and a modified polyethylene terephthalate resin [component (B)] in which 20 mol % of isophthalic acid is copolymerized with 5 mol % of diethylene glycol. Using 100% by mass of this side-by-side type composite staple fiber, a carded web having a basis weight of 30 g/m$^2$ was provided by a carding method.

This carded web was moved on a conveyer net, and allowed to pass between the conveyer net and a porous plate drum with pores (circular form) having a diameter of 2 mmφ and a pitch of 2 mm and being arranged in a hound's-tooth check pattern. From the inside of the porous plate drum, a water flow was injected in a spray form at 0.8 MPa toward the web and the conveyer net, and thus an uneven distribution step for periodically forming a low-density region and a high-density region of fibers was conducted.

Then, the carded web was transferred to a heating step while the web was overfed at about 200% without prevention of contraction in the heating step due to steam.

Then, the carded web was introduced to a steam injecting apparatus provided in a belt conveyer, and steam at 0.5 MPa and a temperature of about 160° C. was ejected to the carded web perpendicularly from the steam injecting apparatus to treat the web with steam, so that coil-shaped crimps of the latently crimped fibers were expressed, and at the same time, the fibers were entangled. In this steam injecting apparatus, nozzles were installed in one of the conveyers so as to blow steam toward the carded web through the conveyer belt. Each of the steam injecting nozzles had a pore diameter of 0.3 mm, and an apparatus in which the nozzles were arranged in a line at a pitch of 2 mm in the width direction of the conveyer was used. The processing speed was 8.5 m/min, and the distance between each nozzle and the conveyor belt on a suction side was 7.5 mm. Finally, the web was dried with hot air at 120° C. for 1 minute to obtain a stretchable fibrous sheet.

Observation of a surface and cross section in the thickness direction of the obtained fibrous sheet under an electron microscope (100 magnifications) revealed that fibers were oriented substantially parallel with the plane direction of the fibrous sheet, and crimped substantially uniformly in the thickness direction.

Example 8

A stretchable fibrous sheet was produced in the same manner as in Example 7 except that the hot air drying temperature was set to 140° C. Observation of a surface and cross section in the thickness direction of the obtained fibrous sheet under an electron microscope (100 magnifications) revealed that fibers were oriented substantially parallel with the plane direction of the fibrous sheet, and crimped substantially uniformly in the thickness direction. In Examples 7 and 8 and Comparative Example 5 to be described later, carded webs used had the same basis weight (30 g/m$^2$).

Comparative Example 5

A stretchable fibrous sheet was produced in the same manner as in Example 7 except that the hot air drying temperature was set to 160° C. Observation of a surface and cross section in the thickness direction of the obtained fibrous sheet under an electron microscope (100 magnifications) revealed that fibers were oriented substantially parallel with the plane direction of the fibrous sheet, and crimped substantially uniformly in the thickness direction.

Comparative Example 6

A commercially available polyurethane meltblown nonwoven fabric ("Meltblown UC0060" manufactured by Kuraray Kuraflex Co., Ltd.) was thermally embossed and bonded at a treatment temperature of 130° C., while being extended 1.5 times, onto one side of a commercially available polyester spunbond nonwoven fabric ("ecule 3201 A" manufactured by Toyobo Co., Ltd.) having a three-layer structure of spunbond nonwoven fiber layer/meltblown nonwoven fiber layer/spunbond nonwoven fiber layer, and the resultant was subjected to gathering by relaxing the extension, so that a stretchable fibrous sheet was produced.

6. Evaluation of Fibrous Sheet (Third Embodiment)

Each of the obtained fibrous sheets was subjected to the following evaluation test.

(Concavo-Convex Fitting Property)

A fibrous sheet having a width of 5 cm was wrapped three times around a forefinger, a wrist, and an ankle while being stretched by 30%, and the fitting property for the shape of surface protrusions and recesses of the joint parts of these sites was evaluated with the following five scores, and an average score of five subjects was obtained.

Score 5: No floating of fibrous sheet was sensed at all convavo portions.
Score 4: Little floating of fibrous sheet was sensed.
Score 3: Slight floating of fibrous sheet was sensed.
Score 2: High degree of floating of fibrous sheet was sensed.
Score 1: Extremely high degree of floating of fibrous sheet was sensed.

TABLE 3

|  |  | Example 7 | Example 8 | Comparative Example 5 | Comparative Example 6 |
|---|---|---|---|---|---|
| Number of average coil crimps | (crimps/mm) | 8.4 | 25.8 | 37.9 | — |
| Average crimp pitch | (μm) | 119 | 39 | 26 | — |
| Average curvature radius | (μm) | 67.8 | 55.1 | 27.7 | — |
| Basis weight | (g/m$^2$) | 91.0 | 138.4 | 182.3 | 165.8 |
| Thickness | (mm) | 1.21 | 1.35 | 1.37 | 1.56 |
| Density | (g/cm$^3$) | 0.08 | 0.10 | 0.13 | 0.11 |
| Bending resistance | MD (mN/200 mm) | 91 | 175 | 237 | 115 |
|  | CD (mN/200 mm) | 148 | 266 | 434 | 847 |

TABLE 3-continued

|  |  | Example 7 | Example 8 | Comparative Example 5 | Comparative Example 6 |
|---|---|---|---|---|---|
| Breaking strength | MD (N/50 mm) | 15.6 | 21.8 | 30.7 | 74.2 |
|  | CD (N/50 mm) | 4.3 | 6.5 | 9.1 | 301.8 |
| Elongation at break | MD (%) | 106 | 159 | 191 | 362 |
|  | CD (%) | 105 | 145 | 161 | 15 |
| Stress at 50% extension | MD (N/50 mm) | 5.17 | 4.33 | 5.62 | 2.1 |
|  | CD (N/50 mm) | 3.03 | 3.14 | 3.83 | — |
| Recovery rate after 50% extension | MD (%) | 95.6 | 94.6 | 88.2 | 96.7 |
|  | CD (%) | 91.6 | 91.3 | 82.6 | — |
| Compression elastic modulus Pe | (%) | 71.1 | 81.5 | 87.1 | 87.5 |
| Curved surface sliding stress | (N/50 mm) | 13.3 | 18.9 | 21.1 | 0.4 |
| Evaluation Concavo-convex fitting property | Average score [Forefinger] | 4.4 | 4.1 | 2.8 | 1.8 |
|  | Average score [Wrist] | 4.6 | 4.0 | 2.7 | 2.2 |
|  | Average score [Ankle] | 4.2 | 4.2 | 2.9 | 2.4 |

REFERENCE SIGNS LIST

1: Sample, 2: Single-sided adhesive tape, 3: winding core, 4: Alligator clip, 5: Weight, 6: Base point, 7: Point located half-circle away from base point, 8: Cut, 9: Jig, 10: Chuck

The invention claimed is:

1. A fibrous sheet that satisfies a formula below:

$$80[\%] \leq \{T_3/(3 \times T_1)\} \times 100 \leq 85[\%];$$

when a thickness of the fibrous sheet measured in accordance with A method specified in JIS L 1913 is defined as $T_1$ [mm], and a thickness of three superimposed fibrous sheets measured under the same conditions is defined as $T_3$ [mm],
wherein the fibrous sheet contains only a nonelastomer material,
the fibrous sheet is a nonwoven fabric,
the nonwoven fabric contains crimped fibers crimped into a coil shape,
the crimped fiber is constituted of a conjugated fiber in which a plurality of resins having different thermal shrinkage factors form a phase structure, and is oriented substantially parallel with the plane direction of the fibrous sheet,
the average curvature radius of circles formed by coils of the crimped fibers is 20 to 200 μm, and
wherein upon forming the fibrous sheet, the fibrous sheet is dried at a temperature in a range from 120° C. to less than 160° C., sufficient to satisfy the formula above.

2. The fibrous sheet according to claim 1,
wherein the fibrous sheet satisfies a formula below:

$$S_2/S_1 \geq 3$$

when a stress at extension at a time of extension in an in-plane first direction at 50% elongation is defined as a stress $S_1$ (N/50 mm) at 50% extension, and a stress at extension at a time of extension in an in-plane second direction orthogonal to the first direction at 50% elongation is defined as a stress $S_2$ (N/50 mm) at 50% extension.

3. The fibrous sheet according to claim 2,
wherein the fibrous sheet has a length direction and a width direction, and the first direction is the width direction.

4. The fibrous sheet according to claim 1,
wherein the fibrous sheet has a basis weight of greater than or equal to 50 g/m².

5. The fibrous sheet according to claim 1,
wherein the fibrous sheet has a compression elastic modulus measured in accordance with JIS L 1913 of less than or equal to 85%.

6. The fibrous sheet according to claim 1,
wherein the fibrous sheet has a curved surface sliding stress of 3 to 30 N/50 mm.

7. The fibrous sheet according to claim 1,
wherein the fibrous sheet is a bandage.

8. The fibrous sheet according to claim 1, wherein the drying is performed at a temperature of from 120° C. to 140° C.

9. The fibrous sheet according to claim 1, wherein the fibrous sheet is dried at a temperature in a range from greater than 120° C. to less than 160° C.

* * * * *